(12) United States Patent
Nebuya et al.

(10) Patent No.: US 10,285,618 B2
(45) Date of Patent: May 14, 2019

(54) EIT MEASUREMENT DEVICE, EIT MEASUREMENT METHOD AND PROGRAM

(71) Applicant: SCHOOL JURIDICAL PERSON KITASATO INSTITUTE, Tokyo (JP)

(72) Inventors: Satoru Nebuya, Sagamihara (JP); So Hifumi, Sagamihara (JP)

(73) Assignee: SCHOOL JURIDICAL PERSON KITASATO INSTITUTE, Tokyo (JP)

( * ) Notice: Subject to any disclaimer, the term of this patent is extended or adjusted under 35 U.S.C. 154(b) by 605 days.

(21) Appl. No.: 14/901,445

(22) PCT Filed: Jul. 1, 2014

(86) PCT No.: PCT/JP2014/067590
§ 371 (c)(1),
(2) Date: Feb. 8, 2016

(87) PCT Pub. No.: WO2015/002210
PCT Pub. Date: Jan. 8, 2015

(65) Prior Publication Data
US 2016/0302690 A1 Oct. 20, 2016

(30) Foreign Application Priority Data
Jul. 2, 2013 (JP) ................. 2013-139164

(51) Int. Cl.
*A61B 5/00* (2006.01)
*A61B 5/053* (2006.01)
*A61B 5/107* (2006.01)

(52) U.S. Cl.
CPC .......... *A61B 5/0536* (2013.01); *A61B 5/1077* (2013.01); *A61B 5/6823* (2013.01);
(Continued)

(58) Field of Classification Search
CPC ... A61B 5/0536; A61B 5/1077; A61B 5/7475; A61B 5/6831; A61B 5/6823;
(Continued)

(56) References Cited

U.S. PATENT DOCUMENTS 6,519,862 B1 * 2/2003 Owsley ................. A61B 5/103
33/501.02
2005/0059903 A1 3/2005 Izumi
(Continued)

FOREIGN PATENT DOCUMENTS

CN 101524273 9/2009
JP 2003-339658 12/2003
(Continued)

OTHER PUBLICATIONS

International Search Resort issued in PCT/JP2014/067590 dated Sep. 16, 2014 (w/ translation).
(Continued)

*Primary Examiner* — Rene T Towa
(74) *Attorney, Agent, or Firm* — Nixon & Vanderhye P.C.

(57) ABSTRACT

An electrical impedance tomography (EIT) measurement device (1) includes a measurement belt (10) to which a plurality of electrode pads arranged in a row and a plurality of strain gauges arranged in parallel to the plurality of electrode pads are integrally adhered and configured to be used after being wrapped around a portion (X) serving as a measurement target of a living body, an EIT measurement control unit configured to acquire a tomographic image of the portion (X) serving as the measurement target while applying a current to the plurality of electrode pads and acquiring a voltage signal generated between the electrode pads, and a contour estimation unit configured to estimate a contour shape of the portion serving as the measurement
(Continued)

target and a size of the contour shape on the basis of curvature data acquired via the strain gauge.

9 Claims, 29 Drawing Sheets

(52) U.S. Cl.
CPC .......... *A61B 5/6831* (2013.01); *A61B 5/7475* (2013.01); *A61B 5/107* (2013.01); *A61B 2560/0252* (2013.01); *A61B 2562/0261* (2013.01); *A61B 2562/043* (2013.01); *A61B 2562/14* (2013.01)

(58) Field of Classification Search
CPC ........ A61B 2562/0261; A61B 2562/14; A61B 2562/043; A61B 2560/0252; A61B 5/107
See application file for complete search history.

(56) References Cited

U.S. PATENT DOCUMENTS

| | | | |
|---|---|---|---|
| 2009/0084674 | A1 | 4/2009 | Holzhacker et al. |
| 2010/0198101 | A1 | 8/2010 | Song et al. |
| 2011/0007937 | A1 | 1/2011 | Yan et al. |
| 2012/0271193 | A1 | 10/2012 | Li et al. |
| 2013/0190577 | A1 | 7/2013 | Brunner et al. |

FOREIGN PATENT DOCUMENTS

| | | |
|---|---|---|
| JP | 2005-152061 | 6/2005 |
| JP | 2009011335 A * | 1/2009 |
| JP | 2009-523037 | 6/2009 |
| JP | 2011-515181 | 5/2011 |
| JP | 2012-61057 | 3/2012 |
| JP | 2012-90880 | 5/2012 |
| JP | 2012-228514 | 11/2012 |
| KR | 10-0598146 | 7/2006 |
| WO | WO 2007/070997 | 6/2007 |
| WO | WO 2009/118701 | 10/2009 |
| WO | WO 2012/045188 | 4/2012 |
| WO | WO 2012/168836 | 12/2012 |

OTHER PUBLICATIONS

Nebuya et al., "Development of a wearable electrical impedance tomography for an evaluation of lung function," *Proceedings of the 27th Symposium on Biological and Physiological Engineering*, Sep. 19-21, 2012, pp. 263-265, 2A2-02, Sapporo, Japan.

Khor et al. Development of a Sensor Network for Dynamic Boundary Measurement in Neonatal Electrical Impedance Tomography (EIT), *International Federation for Medical and Biological Engineering (IFMBE) Proceedings*, vol. 25, No. II: 386-389 (2009).

Supplementary European Search Report issued in App. No. 14820626.1 dated Feb. 13, 2017.

Extended European Search Resort issued in Appln. No. 14820626.1 dated Jul. 14, 2017.

* cited by examiner

EIT MEASUREMENT DEVICE, EIT MEASUREMENT METHOD AND PROGRAM

TECHNICAL FIELD

The present invention relates to an electrical impedance tomography (EIT) measurement device, a method for acquiring a shape of a cross-section, and a program for measuring a tomographic image of a living body.

This application is the U.S. national phase of International Application No. PCT/JP2014/067590 filed on Jul. 1, 2014, which claims priority to Japanese Patent Application No. 2013-139164, filed on Jul. 2, 2013, the entire contents of each of which are hereby incorporated by reference.

BACKGROUND ART

An electrical impedance tomography (hereinafter simply referred to as EIT) measurement device is technology for causing a weak current to flow from pairs of electrodes adhered to a body surface and imaging a conductivity distribution or a distribution of a conductivity change within a living body from a potential difference occurring in the body surface.

EIT has an advantage in that size reduction, long-time measurement, and real-time measurement are facilitated without a problem of radiation exposure as compared with X-ray computed tomography (CT) because it is possible to acquire a tomographic image by applying only a weak current.

In EIT measurement, in general, 8 to 64 electrodes are used. These electrodes are adhered to the periphery of a measurement target portion and connected to a measurement circuit by routing signal cables individually connected to the electrodes. Recently, methods of unifying a plurality of electrodes and signal cables as a module and facilitating the attachment and detachment of the electrodes and the setting of a measurement device have been attempted.

Further, in such methods, technology for connecting a large number of electrode cables used in EIT to electrodes by performing modularization for every two or more pieces or technology for modularizing electrodes for every two or more pieces to simplify a procedure of connecting a required large number of electrodes to a body surface during EIT measurement are proposed (for example, see Patent Literatures 1 and 2).

CITATION LIST

Patent Literatures

[Patent Literature 1]
 Japanese Unexamined Patent Application, First Publication No. 2012-228514
[Patent Literature 2]
 Japanese Unexamined Patent Application, First Publication No. 2009-523037

SUMMARY OF INVENTION

Technical Problem

However, in the above-described EIT measurement, information indicating a positional relation in which a plurality of electrode pads are arranged is not included in a tomographic image generated on the basis of electrical signals acquired through the plurality of electrode pads. That is, the tomographic image generated by the EIT measurement device is generated by virtualizing a relative positional relation between the electrode pads, and an absolute positional relation between coordinate positions in the tomographic image and positions in an actual tomographic image in a measurement target is not specified.

In this case, it is not possible for an operator (a person who performs medical treatment) of the EIT measurement device to accurately diagnose various measurement targets having a different shape or size of a contour on the basis of a generated tomographic image.

On the other hand, even if the operator of the EIT measurement device performs an operation of finding a shape of a measurement target portion by performing an operation of measuring a ratio (referred to as an e value) of a vertical length of the measurement target portion to a horizontal length using a dedicated caliper or the like, there is a possibility not only of labor becoming complicated, but also of a measurement error increasing. In addition, in this technique, it is difficult to handle a patient who cannot easily stand.

The present invention provides an EIT measurement device, an EIT measurement method, and a program capable of performing simple and more accurate diagnosis even for various measurement targets having a different shape or size of a contour.

Solution to Problem

According to a first aspect of the present invention, there is provided an EIT measurement device including: a measurement belt to which a plurality of electrode pads arranged in a row and a plurality of strain gauges arranged in parallel to the plurality of electrode pads are integrally adhered and configured to be used after being wrapped around a portion serving as a measurement target of a living body; an EIT measurement control unit configured to acquire a tomographic image of the portion serving as the measurement target while applying a current to the plurality of electrode pads and acquiring a voltage signal generated between the electrode pads; and a contour estimation unit configured to estimate a contour shape of the portion serving as the measurement target and a size of the contour shape on the basis of curvature data acquired via the strain gauge, wherein the contour estimation unit executes a relative position specifying process of specifying a relative positional relation for every strain gauge and a shape specifying process of specifying the contour shape while coupling by a predetermined function curve between strain gauges between which the relative positional relation is specified on the basis of the curvature data.

According to a second aspect of the present invention, in the above-described EIT measurement device, the contour estimation unit executes a size specifying process of enlarging or reducing the estimated contour shape so that a perimeter of the estimated contour shape matches a separately measured perimeter of the portion serving as the measurement target after the shape specifying process.

According to a third aspect of the present invention, in the above-described EIT measurement device, the contour estimation unit executes, in the relative position specifying process, a first step of specifying a coordinate position of a reference point indicating a position of a strain gauge designated for every predetermined interval at a distance of one or more strain gauges among the plurality of strain gauges arranged in the row as predetermined initial coordinate values; a second step of calculating relative coordinate values indicating a coordinate position of a subordinate point indicating a position of any strain gauge arranged between strain gauges indicated by the reference point for a coordinate position of the reference point on the basis of curvature data acquired via the strain gauge; a third step of changing coordinate positions of one reference point and another reference point so that coordinate positions of a first subordinate point at which a coordinate position is specified from relative coordinate values for the coordinate position of the one reference point and a second subordinate point which is a subordinate point at which a coordinate position is specified from relative coordinate values for the coordinate position of the other reference point and indicates the same strain gauge position as the first subordinate point are closest; and a fourth step of specifying a center point between the first subordinate point and the second subordinate point after the change in the third step as coordinate positions of two subordinate points indicating positions of strain gauges arranged at both sides of a strain gauge indicated by the reference point.

According to a fourth aspect of the present invention, in the above-described EIT measurement device, the contour estimation unit specifies the coordinate position of the reference point indicating the strain gauge arranged on a symmetric axis of the portion serving as the measurement target among the plurality of strain gauges as predetermined initial coordinate values in the first step of the relative position specifying process.

According to a fifth aspect of the present invention, in the above-described EIT measurement device, the contour estimation unit regards the strain gauge as being arranged on the symmetric axis of the portion serving as the measurement target and executes the relative position specifying process when no strain gauge is arranged at a position arranged on the symmetric axis of the portion serving as the measurement target on the measurement belt wrapped around the portion serving as the measurement target.

According to a sixth aspect of the present invention, in the above-described EIT measurement device, the contour estimation unit sets a plurality of supplementary points for specifying a curve connected between a position of one strain gauge and a position of another strain gauge adjacent to the one strain gauge in the shape specifying process, and a distance from an origin of the plurality of supplementary points is determined by a predetermined function at an angle formed by the supplementary points, the origin, and the position of the one strain gauge.

According to a seventh aspect of the present invention, the above-described EIT measurement device includes: a perimeter measurement electrode pad arranged in parallel to the plurality of electrode pads and adhered to the measurement belt; and a perimeter measurement unit configured to measure a perimeter of the portion serving as the measurement target on the basis of a voltage signal acquired via the perimeter measurement electrode pad.

According to an eighth aspect of the present invention, there is provided an EIT measurement method including: winding a measurement belt to which a plurality of electrode pads arranged in a row and a plurality of strain gauges arranged in parallel to the plurality of electrode pads are integrally adhered around a portion serving as a measurement target of a living body; acquiring, by an EIT measurement control unit, a tomographic image of the portion serving as the measurement target while applying a current to the plurality of electrode pads and acquiring a voltage signal generated between the electrode pads; and executing, by a contour estimation unit, a relative position specifying process of specifying a relative positional relation for every strain gauge and a shape specifying process of specifying a contour shape of the portion serving as the measurement target while coupling by a predetermined function curve between strain gauges between which the relative positional relation is specified on the basis of curvature data acquired via the strain gauge and estimating the contour shape and a size of the contour shape.

According to a ninth aspect of the present invention, there is provided a program for causing a computer of an EIT measurement device, which includes a measurement belt to which a plurality of electrode pads arranged in a row and a plurality of curvature sensors arranged in parallel to the plurality of electrode pads are integrally adhered and configured to be used after being wrapped around a portion serving as a measurement target of a living body, to function as: an EIT measurement control means configured to acquire a tomographic image of the portion serving as the measurement target while applying a current to the plurality of electrode pads and acquiring a voltage signal generated between the electrode pads; and a contour estimation means configured to estimate a contour shape of the portion serving as the measurement target and a size of the contour shape on the basis of curvature data acquired via the strain gauge, wherein the contour estimation means executes a relative position specifying process of specifying a relative positional relation for every strain gauge and a shape specifying process of specifying the contour shape while coupling by a predetermined function curve between strain gauges between which the relative positional relation is specified on the basis of the curvature data.

According to a tenth aspect of the present invention, there is provided an EIT measurement device including: a measurement belt to which a plurality of electrode pads arranged in a row and a plurality of strain gauges arranged in parallel to the plurality of electrode pads are integrally adhered and configured to be used after being wrapped around a portion serving as a measurement target of a living body; an EIT measurement control unit configured to acquire a tomographic image of the portion serving as the measurement target while applying a current to the plurality of electrode pads and acquiring a voltage signal generated between the electrode pads; and a contour estimation unit configured to estimate a contour shape of the portion serving as the measurement target and a size of the contour shape on the basis of curvature data acquired via the curvature sensor, wherein the contour estimation unit executes a relative position specifying process of specifying a relative positional relation for every curvature sensor and a shape specifying process of specifying the contour shape while coupling by a predetermined function curve between curvature sensors between which the relative positional relation is specified on the basis of the curvature data.

Advantageous Effects of Invention

It is possible to perform simple and more accurate diagnosis even for various measurement targets having a different shape or size of a contour.

DESCRIPTION OF EMBODIMENTS

First Embodiment

Hereinafter, an EIT measurement device according to the first embodiment will be described with reference to the drawings.

Figure 1:
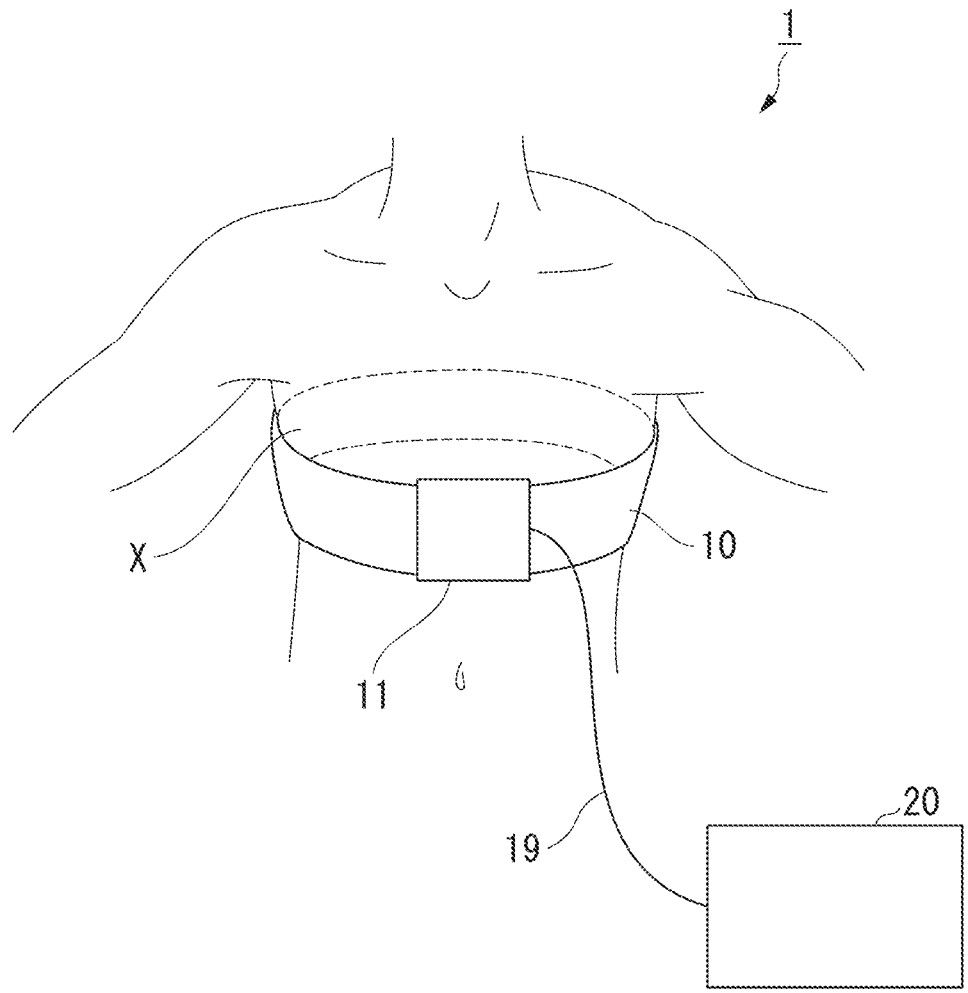
FIG. 1 is a diagram illustrating an entire configuration of an EIT measurement device according to a first embodiment.

FIG. 1 is a diagram illustrating an entire configuration of the EIT measurement device according to the first embodiment. In FIG. 1, the EIT measurement device 1 is illustrated.

The EIT measurement device 1 includes a measurement belt 10 and an EIT measurement main body unit 20. As illustrated in FIG. 1, the measurement belt 10, for example, is wrapped around a portion (hereinafter referred to as a measurement target portion X) serving as a measurement target such as a chest portion of a measurement target person (living body) and used. The measurement belt 10 is connected to the EIT measurement main body unit 20 via a measurement circuit 11 and a signal cable 19.

The measurement belt 10 may be configured with an adjustable wrapping length to be used after being wrapped around a head portion, an arm, a leg, or the like in addition to the chest portion. The measurement belt 10 is configured such that electrode pads for performing EIT measurement, etc. are provided on the same flexible substrate and the electrode pads, etc. can be integrally handled as will be described below (for example, see Japanese Patent Application No. 2010-205988).

The EIT measurement main body unit 20 is a functional unit for performing a predetermined calculation process based on an electrical signal acquired via the measurement belt 10 and the measurement circuit 11 and displaying a tomographic image of a portion (measurement target portion X) of a measurement target person around which the measurement belt 10 is wrapped. An operator of the EIT measurement device 1 can set a condition or the like for EIT measurement via a manipulation input unit provided in the EIT measurement main body unit 20 or recognize a tomographic image via a monitor (image display unit) provided in the EIT measurement main body unit 20. A detailed functional configuration of the EIT measurement main body unit 20 will be described below.

Figure 2:
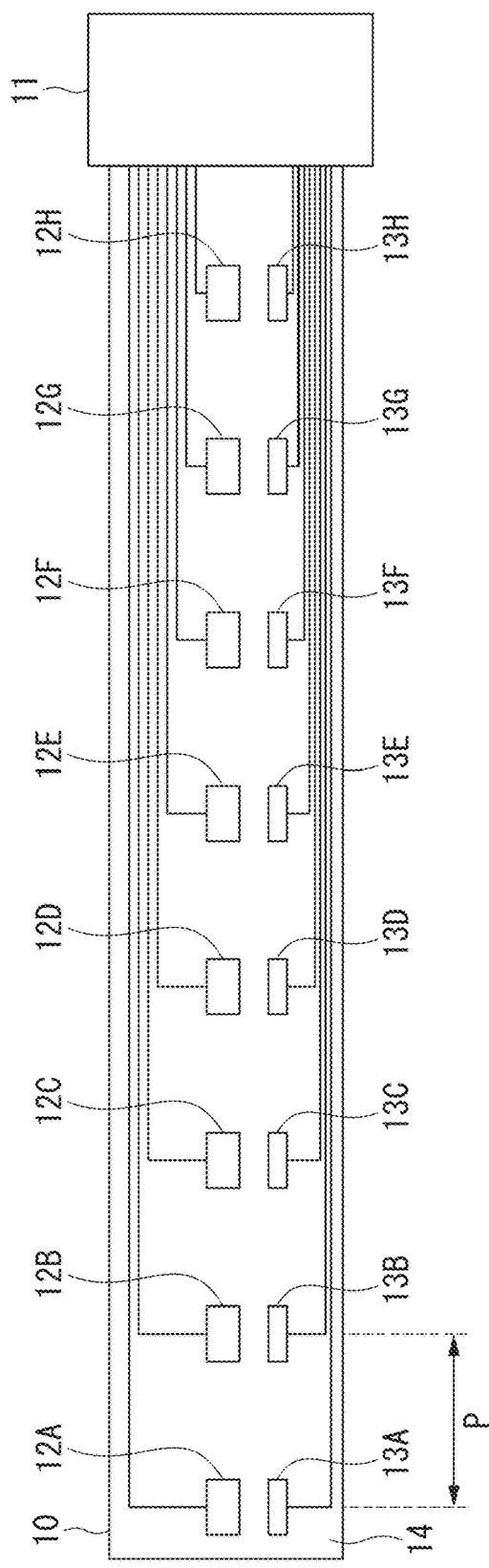
FIG. 2 is a diagram illustrating a functional configuration of a measurement belt according to the first embodiment.

FIG. 2 is a diagram illustrating a functional configuration of the measurement belt according to the first embodiment.

As illustrated in FIG. 2, the measurement belt 10 has a configuration in which eight electrode pads 12A to 12H are disposed (periodically arranged) in a row at distances P of regular intervals on a belt-shaped flexible substrate 14. Also, eight strain gauges 13A to 13H are periodically arranged at distances P of regular intervals in parallel to the eight electrode pads 12A to 12H on the same flexible substrate 14.

The measurement belt 10 is used after being wrapped around the measurement target unit X of the measurement target person while the plurality of electrode pads 12A to 12H and the strain gauges 13A to 13H are integrally adhered. When the measurement belt 10 is wrapped, the electrode pads 12A to 12H have a mechanism in contact with a body surface around the periphery of the measurement target portion X.

Through this configuration, it is possible to significantly reduce the time and effort spent attaching the electrode pads and improve operation efficiency of EIT measurement because the operator of the EIT measurement device 1 can start measurement by merely performing an operation of attaching the measurement belt 10 by wrapping the measurement belt 10 around the measurement target portion X.

Also, the measurement belt 10 may be formed with the flexible substrate 14 further covered with non-conductive belt-like fabric to reduce a burden on the measurement target person during measurement.

In addition, in this case, in the measurement belt 10, a portion in contact with the electrode pads 12A to 12H in the above-described fabric belt is constituted of a conductive gel or a conductive fiber electrode, and the measurement device 1 may perform EIT measurement via the conductive gel or the conductive fiber electrode between the electrode pads 12A to 12H and the body surface. Accordingly, the components of the measurement belt 10 can be configured so that only the fabric portion can be extracted to be washed or disposed of and the usability in terms of hygiene can be further improved.

In addition, the measurement belt 10 may have a strain gauge of the same characteristic at the same position of a backside of each of the strain gauges 13A to 13H. It is possible to implement temperature correction automation, high sensitivity, and high accuracy of the strain gauges 13A to 13H using a two-active-gauge method of connecting a pair of strain gauges of each measurement position to one bridge circuit.

Alternatively, the measurement belt 10 may have the temperature sensor at the same position of the backside of each of the strain gauges 13A to 13H. The measurement device 1 may perform temperature correction of curvature data on the basis of temperature data acquired by the temperature sensor in terms of curvature data acquired by the strain gauges 13A to 13H. Accordingly, it is possible to implement high sensitivity and high accuracy of the strain gauges 13A to 13H.

Also, the measurement circuit 11 is an electrical circuit configured to mediate the exchange of an electrical signal with the EIT measurement main body unit 20, the electrode pads 12A to 12H, and the strain gauges 13A to 13H. For example, in the measurement circuit 11, a circuit configured to amplify the electrical signal output in the strain gauges 13A to 13H or perform analog/digital (A/D) conversion on the electrical signal is provided.

Figure 3:
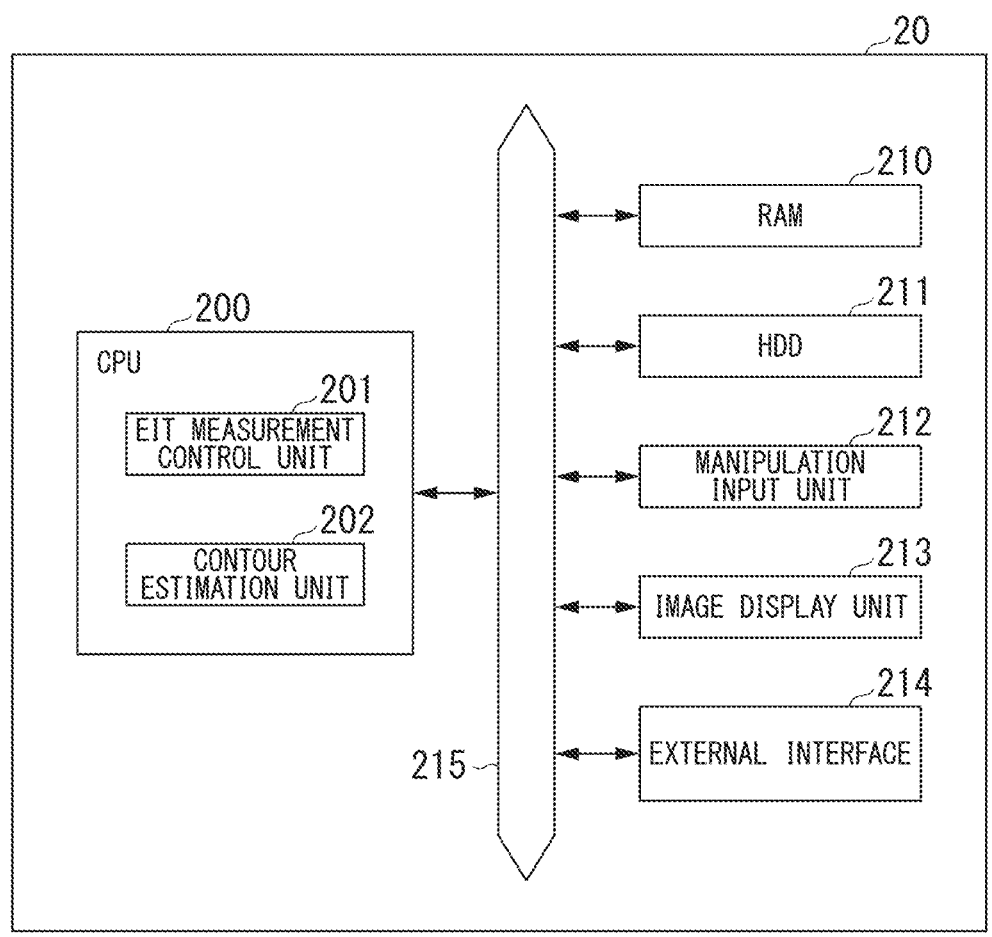
FIG. 3 is a diagram illustrating a functional configuration of an EIT measurement main body according to the first embodiment.

FIG. 3 is a diagram illustrating a functional configuration of an EIT measurement main body according to the first embodiment.

The EIT measurement main body unit 20 according to this embodiment is constituted of a general-purpose personal computer (PC) or a general peripheral device (PC monitor or the like).

As illustrated in FIG. 3, the EIT measurement main body unit 20 includes a central processing unit (CPU) 200 responsible for overall operation, a random access memory (RAM) 210 serving as a work area of the CPU 200 when a measurement program or the like for use in EIT measurement is executed, and a hard disk drive (HDD) 211 serving as a storage means configured to store various programs and a tomographic image, etc. acquired by the EIT measurement control unit 201.

Also, a manipulation input unit 212, for example, is constituted of a mouse, a keyboard, a touch panel, etc. and receives inputs of various types of manipulations by the operator. The image display unit 213 is a liquid crystal display or the like, and displays necessary information during EIT measurement, an acquired tomographic image, etc.

An external interface 214 is a communication interface for performing communication with the external device. In particular, in this embodiment, the external interface 214 is a functional unit connected to the measurement belt 10 via a dedicated communication cable and acquires various signals from the measurement belt 10.

The CPU 200, the RAM 210, the HDD 211, the manipulation input unit 212, the image display unit 213, and the external interface 214 are mutually electrically connected via a system bus 215.

As illustrated in FIG. 3, the CPU 200 performs functions as the EIT measurement control unit 201 and the contour estimation unit 202 while a predetermined measurement program is executed.

The EIT measurement control unit 201 acquires a tomographic image of a measurement target portion X while applying a current to the plurality of electrode pads 12A to 12H and acquiring voltage signals generated between the electrode pads 12A to 12H.

In addition, the contour estimation unit 202 estimates a contour shape of the measurement target portion X and a size of the contour shape on the basis of the curvature data acquired via the strain gauges 13A to 13H.

Figure 4:
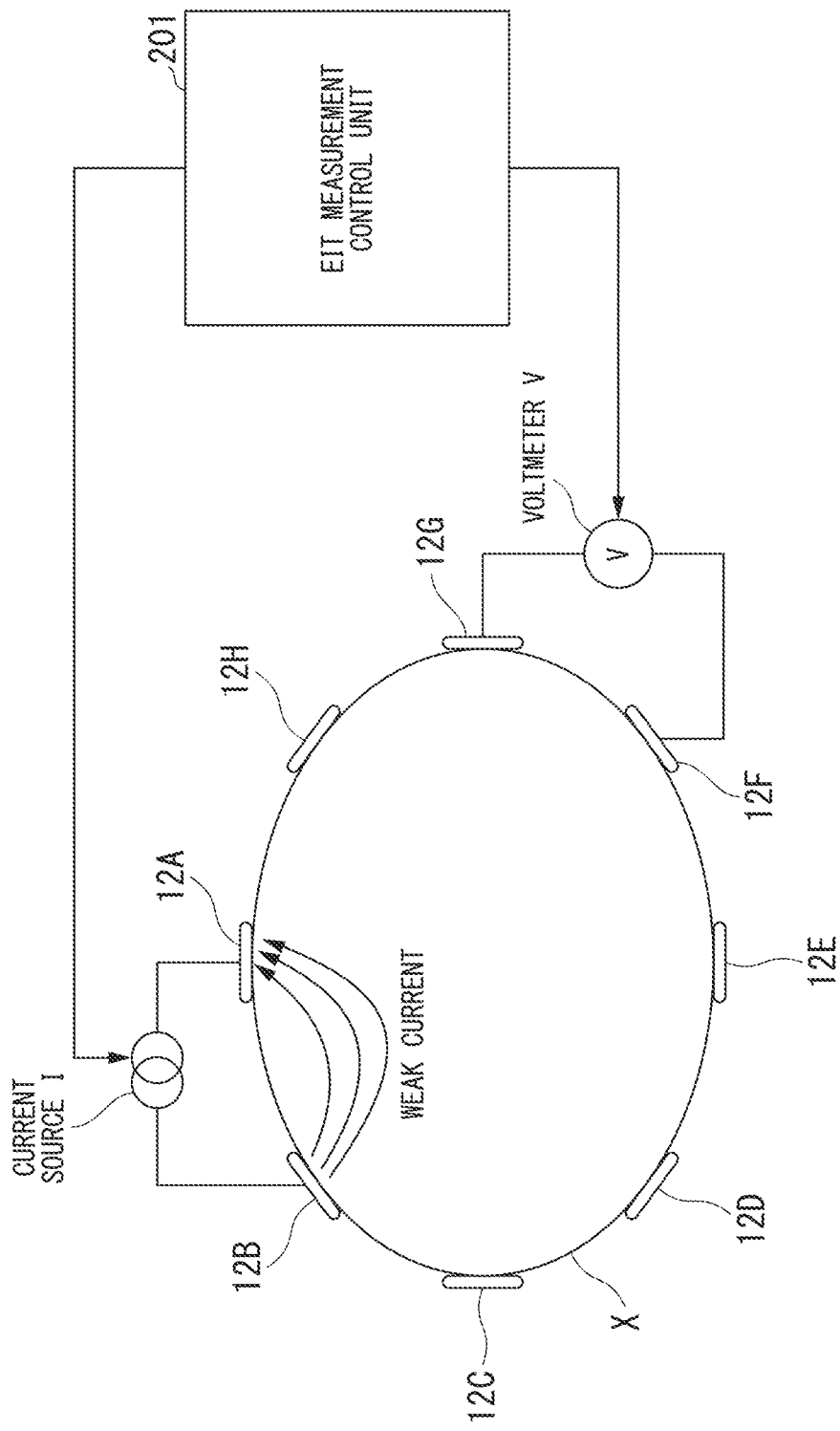
FIG. 4 is a first diagram illustrating a function of an EIT measurement control unit according to the first embodiment.

FIG. 4 is a first diagram illustrating a function of an EIT measurement control unit according to the first embodiment.

Figure 5:
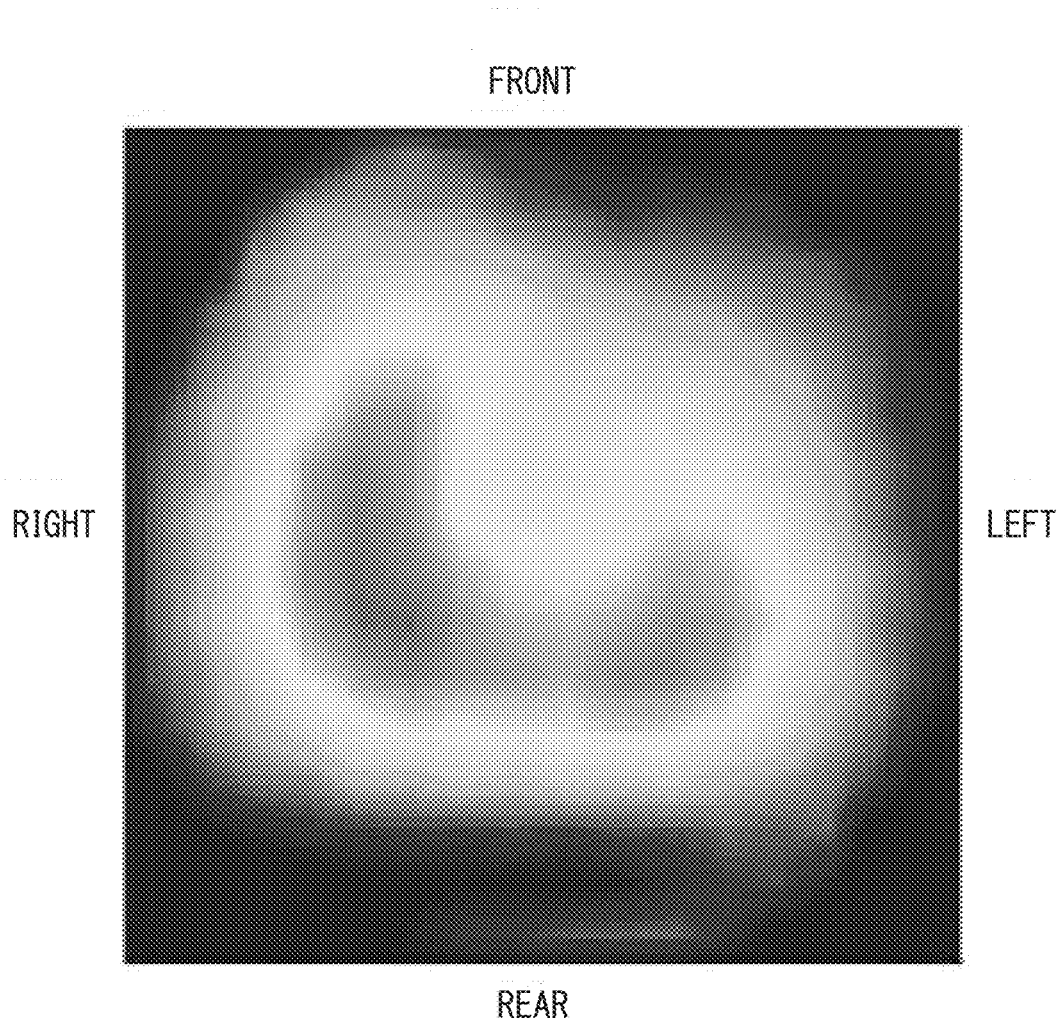
FIG. 5 is a second diagram illustrating a function of the EIT measurement control unit according to the first embodiment.

Also, FIG. 5 is a second diagram illustrating a function of the EIT measurement control unit according to the first embodiment.

Hereinafter, the function of the EIT measurement control unit 201 will be described with reference to FIGS. 4 and 5. FIG. 4 illustrates, for example, a state in which the measurement belt 10 is wrapped around the chest of the measurement target person and the electrode pads 12A to 12H are in contact with the body surface as an example of the measurement target portion X. As illustrated in FIG. 4, a configuration in which a current source I and a voltmeter V are connected between the electrode pads 12A to 12H is formed and the EIT measurement control unit 201 has a function of controlling the current source I and the voltmeter V.

The EIT measurement control unit 201 controls a predetermined weak current to flow between a pair of electrode pads (for example, between the electrode pads 12A and 12B) among the electrode pads 12A to 12H via the current source I. The EIT measurement control unit 201 measures potential differences occurring between the other electrode pads (electrode pads 12C to 12H) via the voltmeter V while the weak current flows through the pair of electrode pads. It is possible to acquire a resistivity distribution in a fault of the measurement target portion X by sequentially changing and rotating the electrode pads through which the current flows to the electrode pads 12B and 12C, 12C and 12D, . . . .

The EIT measurement control unit 201, for example, generates a tomographic image using a general reverse projection method on the basis of a resistivity distribution in a fault plane serving as a measurement target acquired as described above. The EIT measurement control unit 201 allows the operator to view a tomographic image by displaying the generated tomographic image on the image display unit 213. Also, well-known technology may be used as a technique of generating the tomographic image in the EIT measurement control unit 201.

FIG. 5 illustrates an example of the tomographic image generated by the EIT measurement control unit 201. FIG. 5 is a tomographic image in a chest portion of the measurement target person acquired by the EIT measurement control unit 210 and shows a darker shade in a region having higher electrical impedance. According to FIG. 5, a state in which lung fields from which electrical impedance is highly measured according to the presence of air are located on the left and right can be seen.

Also, as a technique in which the EIT measurement control unit 201 generates the tomographic image, a technique using a finite element method (FEM) in addition to the above-described reverse projection method or a technique of combining the finite element method and the reverse projection method is considered. The EIT measurement control unit 201 can image only a relative change based on a certain state when the reverse projection method is used, or can form a tomographic image based on absolute electrical resistivity [Ωm] in a fault plane by using the finite element method.

The tomographic image acquired as in FIG. 5 is generated only on the basis of electrical signals acquired via the electrode pads 12A to 12H, and does not include information indicating any positional relation in which the electrode pads 12A to 12H are actually arranged. That is, the tomographic image is only a tomographic image generated by virtualizing a relative positional relation between the electrode pads 12A to 12H.

Accordingly, because an absolute positional relation between each coordinate position in the tomographic image and each position in an actual fault plane is not specified in a measurement target in the tomographic image acquired by the EIT measurement control unit 201, the operator is not able to perform accurate diagnosis on the basis of the tomographic image.

Therefore, the EIT measurement device 1 according to this embodiment first performs a process of estimating a shape of a contour of the fault plane of the measurement target portion X using the strain gauges 13A to 13H provided in the measurement belt 10 and the contour estimation unit 202. The above-described EIT measurement control unit 201 generates the tomographic image based on the shape of the contour estimated by the contour estimation unit 202.

Figure 6:
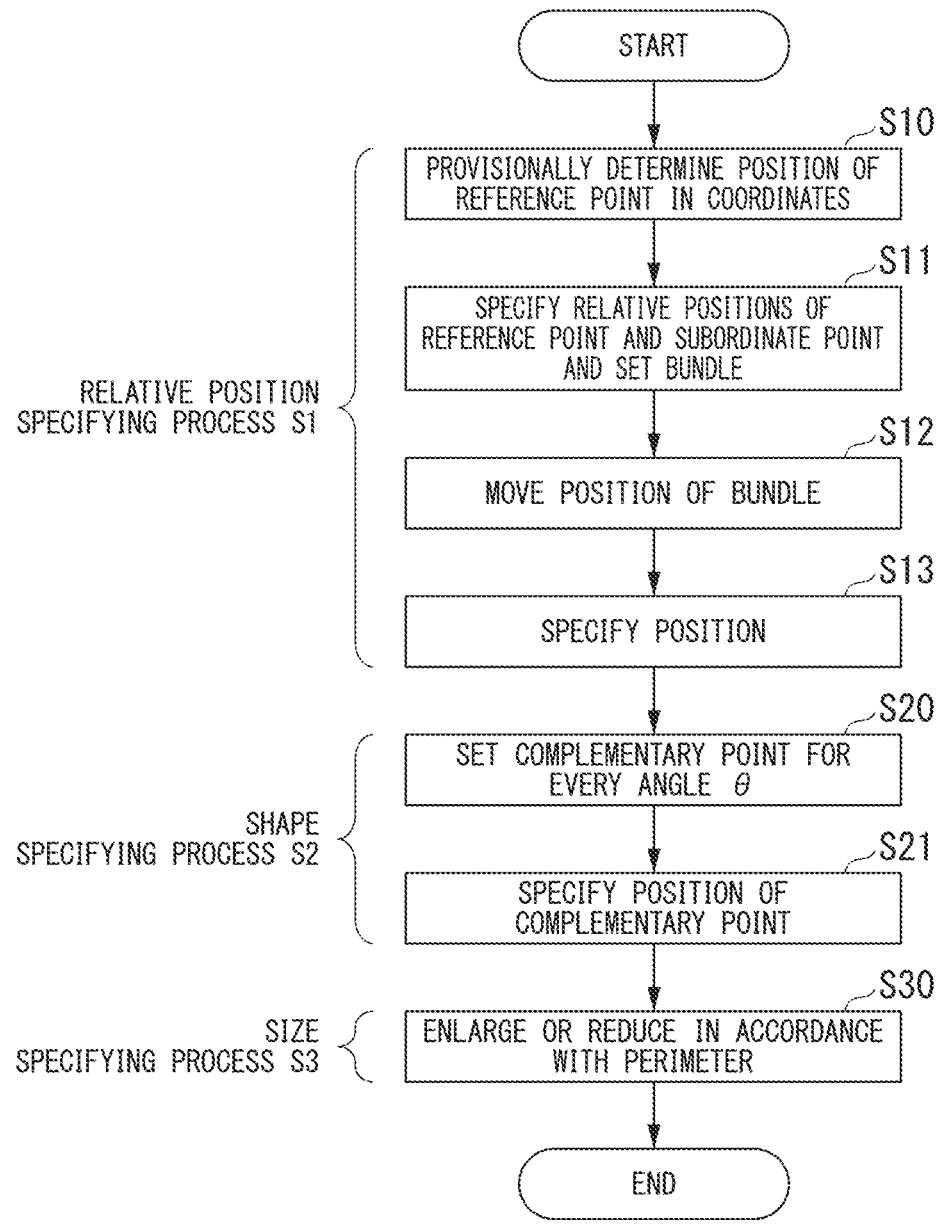
FIG. 6 is a diagram illustrating a processing flow of a contour estimation unit according to the first embodiment.

FIG. 6 is a diagram illustrating a processing flow of the contour estimation unit according to the first embodiment.

Also, FIGS. 7 to 15 are first to ninth diagrams illustrating specific content of each process.

Next, a process in which the contour estimation unit 202 according to this embodiment estimates a contour shape of a fault plane of the measurement target portion X will be specifically described.

As illustrated in FIG. 6, the contour estimation unit 202 estimates a contour shape of the measurement target portion X and a size of the contour shape through a relative position specifying process S1, a shape specifying process S2, and a size specifying process S3. Hereinafter, content of the processes S1 to S3 will be described in detail with reference to FIGS. 6 and 7 to 15.

(Relative Position Specifying Process)

First, the contour estimation unit 202 specifies the relative positional relation for each of the strain gauges 13A to 13H in the relative position specifying process S1.

Figure 7:
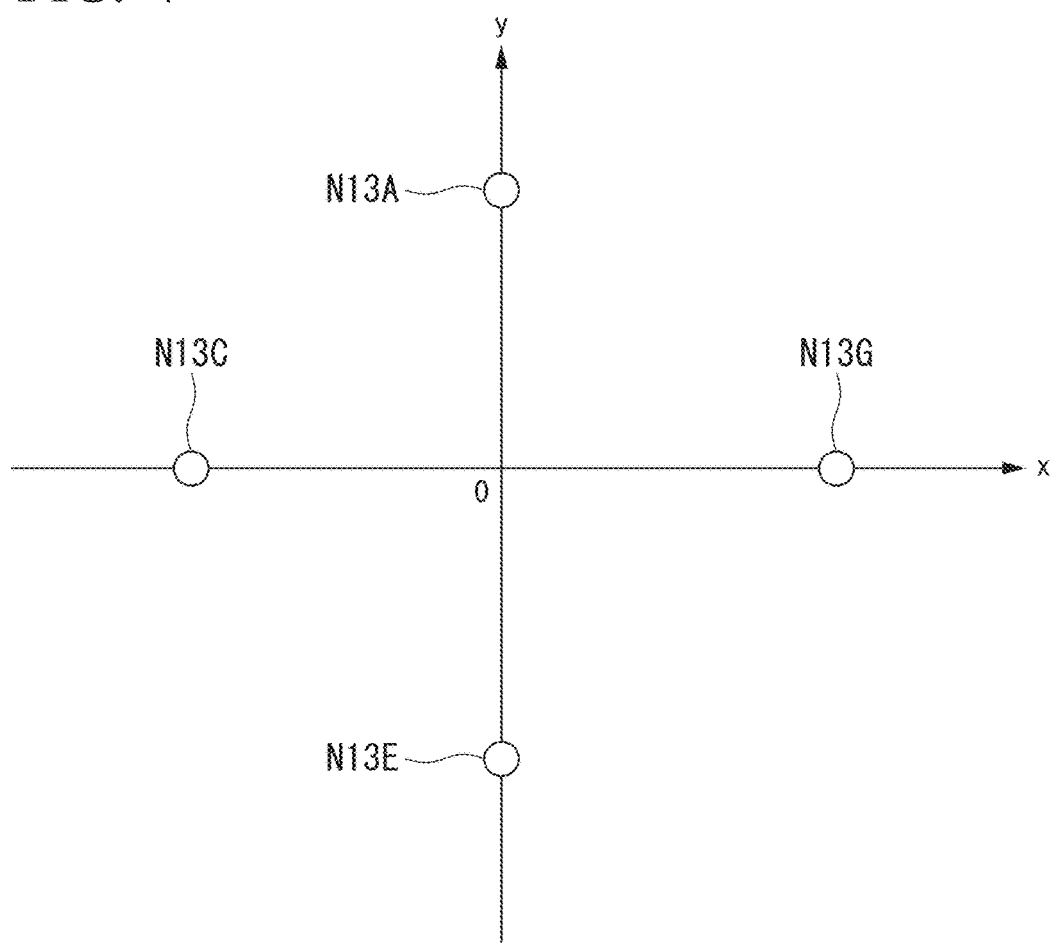
FIG. 7 is a first diagram illustrating specific content of a process of the contour estimation unit according to the first embodiment.

Specifically, as illustrated in FIG. 7, in the first step S10 (FIG. 6), the contour estimation unit 202 first performs a process of setting predetermined xy coordinates and provisionally determining reference points N13A, N13C, N13E, and N13G virtually indicating coordinate positions of the xy coordinates for alternately designated strain gauges (strain gauges 13A, 13C, 13E, and 13G) among the strain gauges 13A to 13H disposed in a row in a longitudinal direction of the measurement belt 10 on the predetermined xy coordinates.

Here, the contour estimation unit 202 specifies coordinate positions of the reference points N13A, N13C, N13E, and N13G up, down, left, and right on x- and y-axes around an origin O, for example, as illustrated in FIG. 7, in the above-described provisional determination process. Specifically, the contour estimation unit 202, for example, reads initial coordinate values pre-stored for each of the reference points N13A to N13G from the HDD 211 and sets the initial coordinate values on coordinates around the origin O. Here, for example, the initial coordinate values for the reference point N13A are stored as (0 [cm], 50 [cm]), the initial coordinate values for the reference point N13C are stored as (−50 [cm], 0 [cm]), the initial coordinate values for the reference point N13E are stored as (0 [cm], −50 [cm]), the initial coordinate values for the reference point N13G are stored as (50 [cm], 0 [cm]), etc.

Next, in a second step S11 (FIG. 6), the contour estimation unit 202 specifies a relative positional relation between the reference points N13A to N13G and subordinate points virtually indicating positions of two strain gauges arranged at both sides of each of the strain gauges 13A to 13G indicated by the reference points N13A to N13G.

Also, a combination of one reference point (for example, N13A) and two subordinate points (for example, N13B1 and N13H2) of both sides of the reference point associated through a relative positional relation is defined as a "bundle" of one set.

In the second step S11, the contour estimation unit 202 specifies a relative positional relation from the reference point N13A by designating points virtually indicating positions of the strain gauges 13B and 13H arranged at both sides of the strain gauge 13A when the measurement belt 10 is wrapped around the measurement target person as subordinate points N13B1 and N13H2 with respect to the reference point N13A indicating a position of the strain gauge 13A. Here, when a relative positional relation of each subordinate point for the reference point is specified, the contour estimation unit 202 receives and refers to curvature data acquired from the strain gauges 13A to 13H from the measurement device 11.

Figure 8:
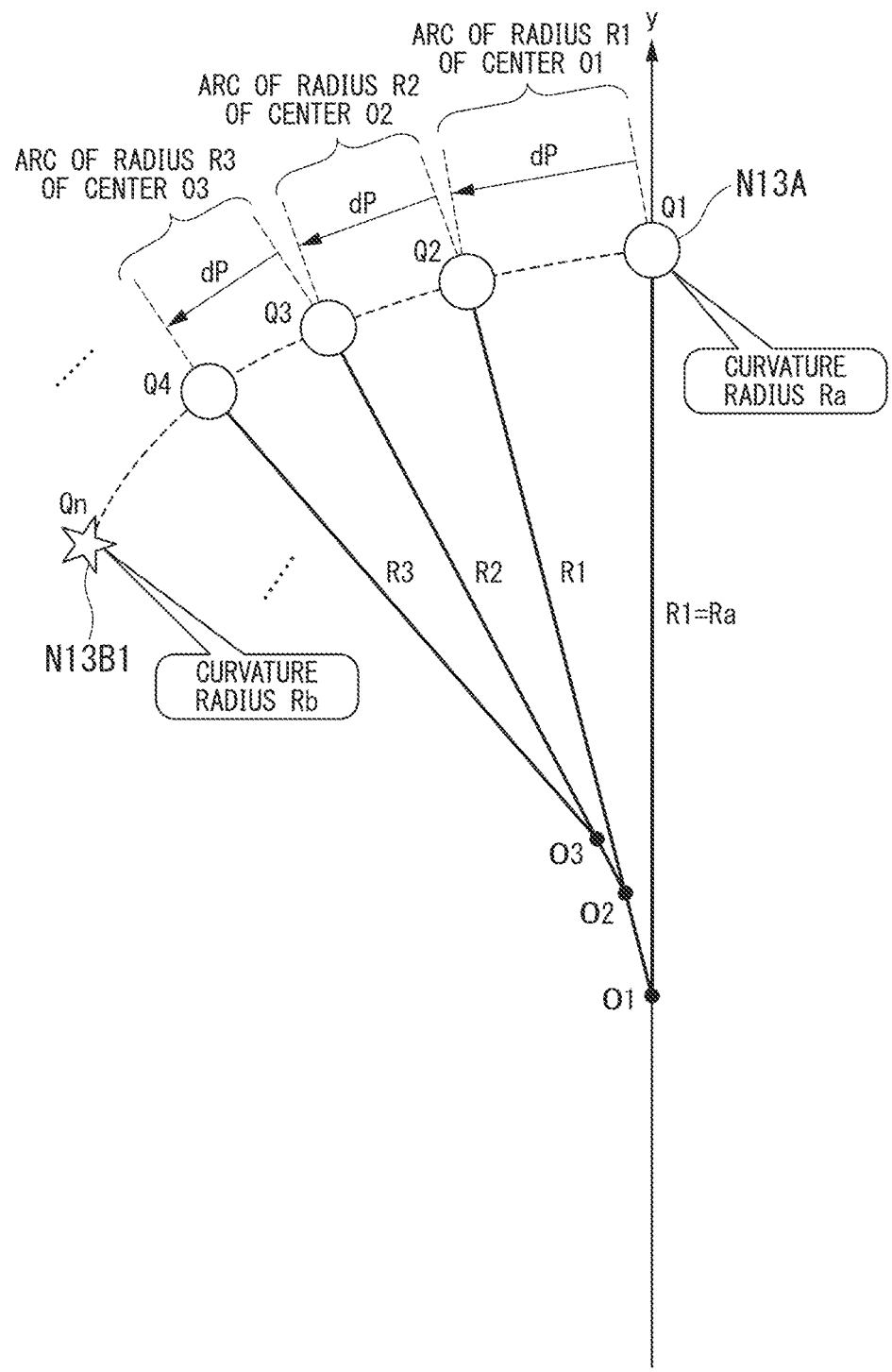
FIG. 8 is a second diagram illustrating specific content of a process of the contour estimation unit according to the first embodiment.

FIG. 8 illustrates a specific process in which the contour estimation unit 202 specifies a relative positional relation of a subordinate point N13B1 for a reference point N13A as an example.

First, the HDD 211 stores an interval between the strain gauge 13A and the strain gauge 13B as a distance P as known data. The contour estimation unit 202 reads the distance P indicating the interval between the strain gauge 13A and the strain gauge 13B by referring to the HDD 211. In addition, the contour estimation unit 202 acquires a curvature radius at each arrangement position from curvature data detected by the strain gauges 13A and 13B.

Here, it is assumed that a curvature radius at a position at which the strain gauge 13A is arranged is Ra and a curvature radius at a position at which the strain gauge 13B is arranged is Rb.

Next, the contour estimation unit 202 calculates a preset micro distance dP on the basis of a distance P indicating an interval between the strain gauge 13A and the strain gauge 13B. This micro distance dP is obtained by sub-dividing a distance P of an interval at which the strain gauges 13A to 13H are arranged into n equal parts (n is an integer of 2 or more). The contour estimation unit 202 specifies a coordinate position of a point Q2 close to the subordinate point N13B1 by a distance dP from a point Q1 (FIG. 8) at which the reference point N13A is arranged. Here, the contour estimation unit 202 specifies a center O1 determined by the curvature radius R1 based on the point Q1 on a straight line connected between the point Q1 (=reference point N13A) and the origin O from the fact that the curvature radius at the point Q1 (=reference point N13A) is R1 (=Ra) and specifies a coordinate position of the point Q2 separated a micro distance dP in a direction of the subordinate point N13B1 from the point Q1 as a point on an arc determined by the center O1 and the radius R1 (see FIG. 8).

Also, the contour estimation unit 202 may perform a process of specifying a coordinate position of the point Q2 by approximating the micro distance dP between the point Q1 and the point Q2 to a distance of a straight line between the point Q1 and the point Q2 without setting the micro distance dP as a length of an arc when the micro distance dP is set to be sufficiently small.

Next, the contour estimation unit 202 calculates a curvature radius R2 at the point Q2 by assuming that the curvature radius gradually changes from Ra to Rb from the reference point N13A to the subordinate point N13B1. For example, when the micro distance dP is set by dividing the distance P into n equal parts, the contour estimation unit 202 calculates the curvature radius R2 at the point Q2 according to a formula of R2=Ra+(Rb−Ra)/n.

Next, the contour estimation unit 202 specifies a coordinate position of a point Q3 close to the subordinate point N13B1 by a micro distance dP from the point Q2. Here, the contour estimation unit 202 specifies a center O2 determined by the curvature radius R2 based on the point Q2 on a straight line connected between the point Q2 and the center O1 from the fact that the curvature radius at the point Q2 is R2 and specifies a coordinate position of the point Q3 separated by a micro distance dP in a direction of the subordinate point N13B1 from the point Q2 as a point on an arc determined by the center O2 and the radius R2 (see FIG. 8).

The contour estimation unit 202 specifies Q3, Q4, ... and a coordinate position for every micro distance dP while iterating the above process and determines a point Qn when a sum of micro distances dP is a distance P as the subordinate point N13B1. Also, a general formula for obtaining a curvature radius Ri at a point Q1 (1≤i≤n) is given as Ri=Ra+(Rb−Ra)×i/n.

Through the above process, relative coordinate values for the subordinate point N13B1 indicating the relative positional relation between the reference point N13A and the subordinate point N13B1 are specified. Likewise, the contour estimation unit 202 specifies relative coordinate values for the subordinate point N13H2. Thus, the contour estimation unit 202 associates the reference point N13A for which a relative positional relation is specified and two subordinate points N13B1 and N13H2 as a bundle of one set.

Through the above-described process, the contour estimation unit 202 can specify a relative positional relation of a subordinate point for a reference point under the assumption that an actual shape of a body surface is precisely reflected (the assumption that the curvature radius at each point between the strain gauges moderately changes).

Figure 9:
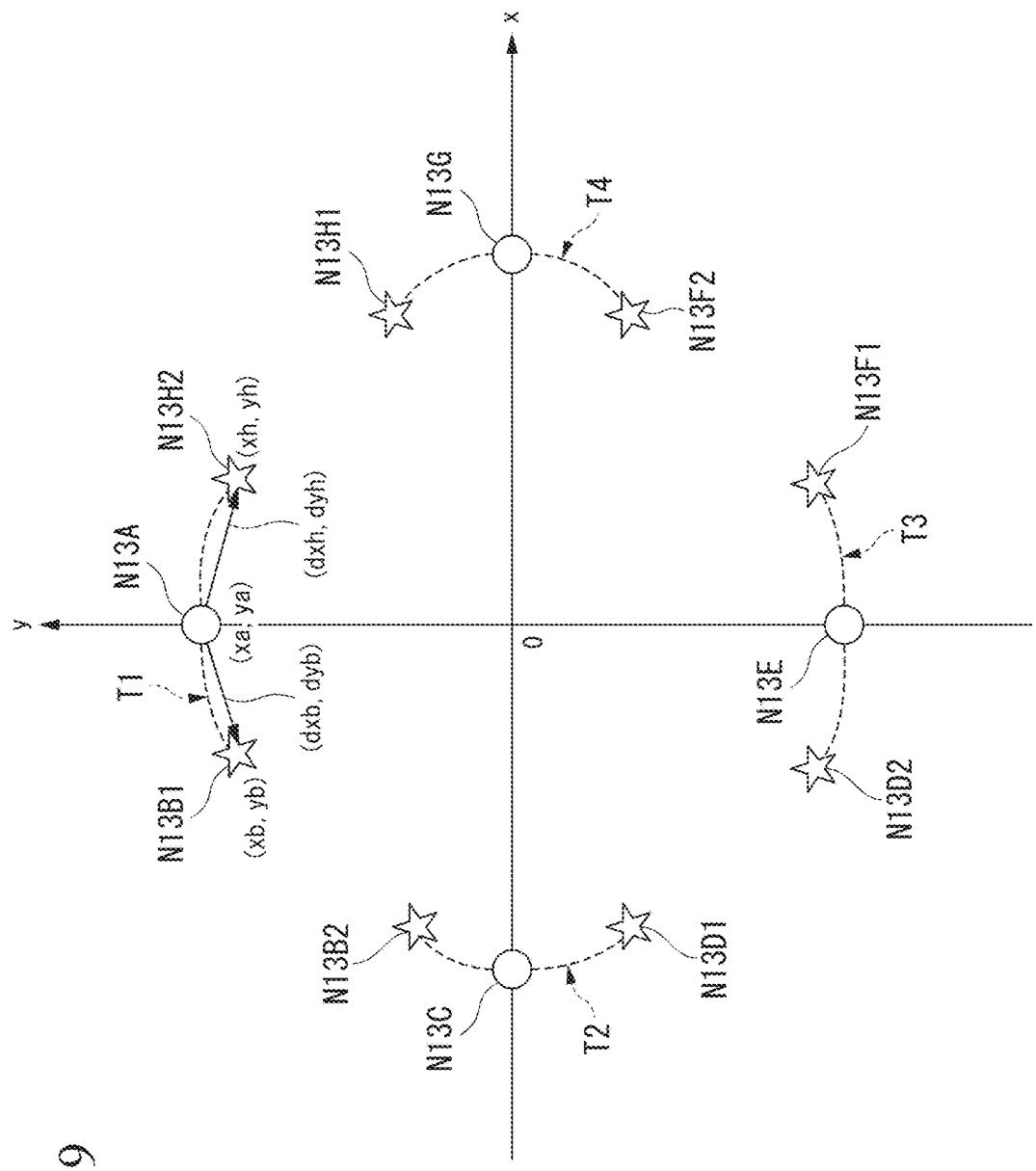
FIG. 9 is a third diagram illustrating specific content of a process of the contour estimation unit according to the first embodiment.

FIG. 9 is a diagram illustrating the reference points N13A to N13G and the subordinate points N13B1 to N13H2 related to the reference points N13A to N13G on the xy coordinates.

As illustrated in FIG. 9, the contour estimation unit 202 specifies coordinate positions (xb, yb) and (xh, yh) of the two subordinate points N13B1 and N13H2 from the relative coordinate values (dxb, dyb) and (dxh, dyh) based on the coordinate position (xa, ya) of the reference point N13A. The contour estimation unit 202 associates a coordinate position (xa, ya) of the reference point N13A and coordinate positions (xb, yb) and (xh, yh) of the two subordinate points N13B1 and N13H2 as information of a bundle T1 and temporarily stores the information in the RAM 210. In this step, the coordinate position (xb, yb) of the subordinate point N13B1 can be calculated by xb=xa+dxb and yb=xa+dyb.

As described above, in the bundle T1, the relative positional relation between the reference point N13A and the two subordinate points N13B1 and N13H2 associated with the reference point N13A is specified.

Likewise, the contour estimation unit 202 associates information of a coordinate position of the reference point N13C with information of coordinate positions of the two subordinate points N13D1 and N13B2 associated with the reference point N13C as information of a bundle T2 and temporarily stores the information in the RAM 210.

Further, the contour estimation unit 202 associates information of coordinate positions of the reference points N13E and N13G and information of coordinate positions of the two subordinate points N13F1 and N13D2 and the two subordinate points N13H1 and N13F2 associated with the reference points N13E and N13G as information of a bundle T3 and a bundle T4 and temporarily stores the information in the RAM 210.

Here, as described above, in the bundle T1, the subordinate point N13B1 is a point virtually indicating the position of the strain gauge 13B arranged adjacent to the strain gauge 13A. On the other hand, in the bundle T2, the subordinate point N13B2 is a point virtually indicating the position of the strain gauge 13B arranged adjacent to the strain gauge 13C.

Assuming that only one electrode pad is located between strain gauges corresponding to a position of the reference point and the total number of electrode pads adhered to the body is eight, the two subordinate points N13B1 and N13B2 belonging to different bundles (T1 or T2) indicate the position of the same strain gauge 13B. Therefore, in this case, the two subordinate points N13B1 (first subordinate point) and N13B2 (second subordinate point) are originally considered to be indicated by the same coordinate position.

In addition, in FIG. 9, the subordinate point N13D1 belonging to the bundle T2 and the subordinate point N13D2 belonging to the bundle T3 indicate the position of the same strain gauge 13D. Likewise, the subordinate points N13F1 and N13F2 indicate the position of the same strain gauge 13F and the subordinate points N13H1 and N13H2 indicate the position of the same strain gauge 13H.

Therefore, similar ideas are established for the subordinate points N13D1 and N13D2, the subordinate points N13F1 and N13F2, and the subordinate points N13H1 and N13H2.

Here, as the third step S12, the contour estimation unit 202 performs a process of moving a position on xy coordinates by changing coordinate positions of points (a reference point and a subordinate point) included in each of the bundles T1 and T2 so that the subordinate point N13B1 included in the bundle T1 matches the subordinate point N13B2 which is the subordinate point included in the bundle T2 and indicates the position of the same strain gauge 13B as the subordinate point N13B1 included in the bundle T1. At this time, the contour estimation unit 202 changes a coordinate position of each point while a relative positional relation between a reference point and a subordinate point included in each of the bundle T1 and the bundle T2 is maintained.

Figure 10:
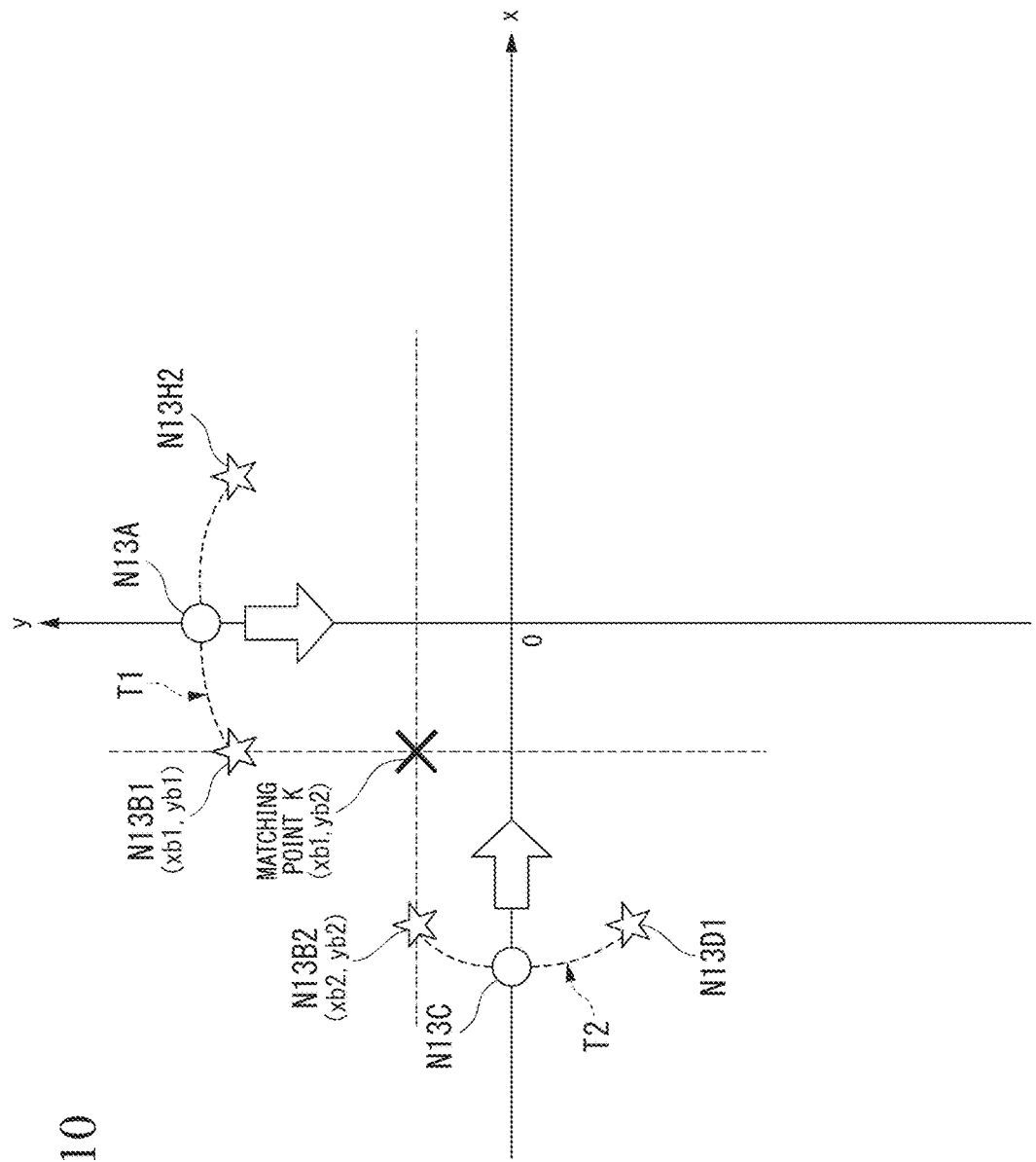
FIG. 10 is a fourth diagram illustrating specific content of a process of the contour estimation unit according to the first embodiment.

FIG. 10 illustrates a process in which the contour estimation unit 202 causes coordinate positions of the subordinate points N13B1 and N13B2 indicating the position of the same strain gauge 13B to match by changing coordinate positions of points (a reference point and a subordinate point) included in the bundle T1 and the bundle T2. Specifically, as illustrated in FIG. 10, the contour estimation unit 202 performs a process of changing a coordinate position to move the bundle T1 along the y axis in parallel. The term "to move in parallel," for example, indicates a process of adding or subtracting the same value even for y coordinate values of the subordinate points N13B1 and N13H2 simultaneously when the coordinate position is changed by adding a predetermined value to the y coordinate value of the reference point N13A or subtracting the predetermined value from the y coordinate value of the reference point N13A and changing a coordinate position while maintaining a relative positional relation of each point. However, the contour estimation unit 202 can perform a process of changing a coordinate position to move the bundle T1 in parallel by substantially performing a process of changing only the coordinate position of the reference point N13A because coordinate positions of the subordinate points N13B1 and N13H2 are specified according to relative coordinate values based on a coordinate position of the reference point N13A in this embodiment.

Likewise, the contour estimation unit 202 performs a process of changing the coordinate position to move the bundle T2 to the origin O in parallel along the x-axis.

Here, when the bundles T1 and T2 are moved in parallel along the y-axis and the x-axis, the contour estimation unit 202 specifies a coordinate position of a matching point K (FIG. 10) at which the subordinate points N13B and N13B2 overlap. Here, the contour estimation unit 202 specifies the coordinate position of the matching point K as (xb1, yb2) when a coordinate position at a current time point of the subordinate point N13B1 is (xb1, yb1) and a coordinate position at a current time point of the subordinate point N13B2 is (xb2, yb2).

The contour estimation unit 202 performs a process of calculating a difference (yb1−yb2) between the y coordinate values of each subordinate point N13B1 and the matching point K and subtracting the difference (yb1−yb2) from the y coordinate value of the reference point N13A included in the bundle T1. Likewise, the contour estimation unit 202 performs a process of calculating a difference (xb1−xb2) between the x coordinate values of each subordinate point N13B2 and the matching point K and adding the difference (xb1−xb2) to the x coordinate value of the reference point N13C included in the bundle T2.

Thus, the contour estimation unit 202 changes coordinate positions of the bundles T1 and T2 so that coordinate positions of the subordinate points N13B1 and N13B2 match.

Figure 11:
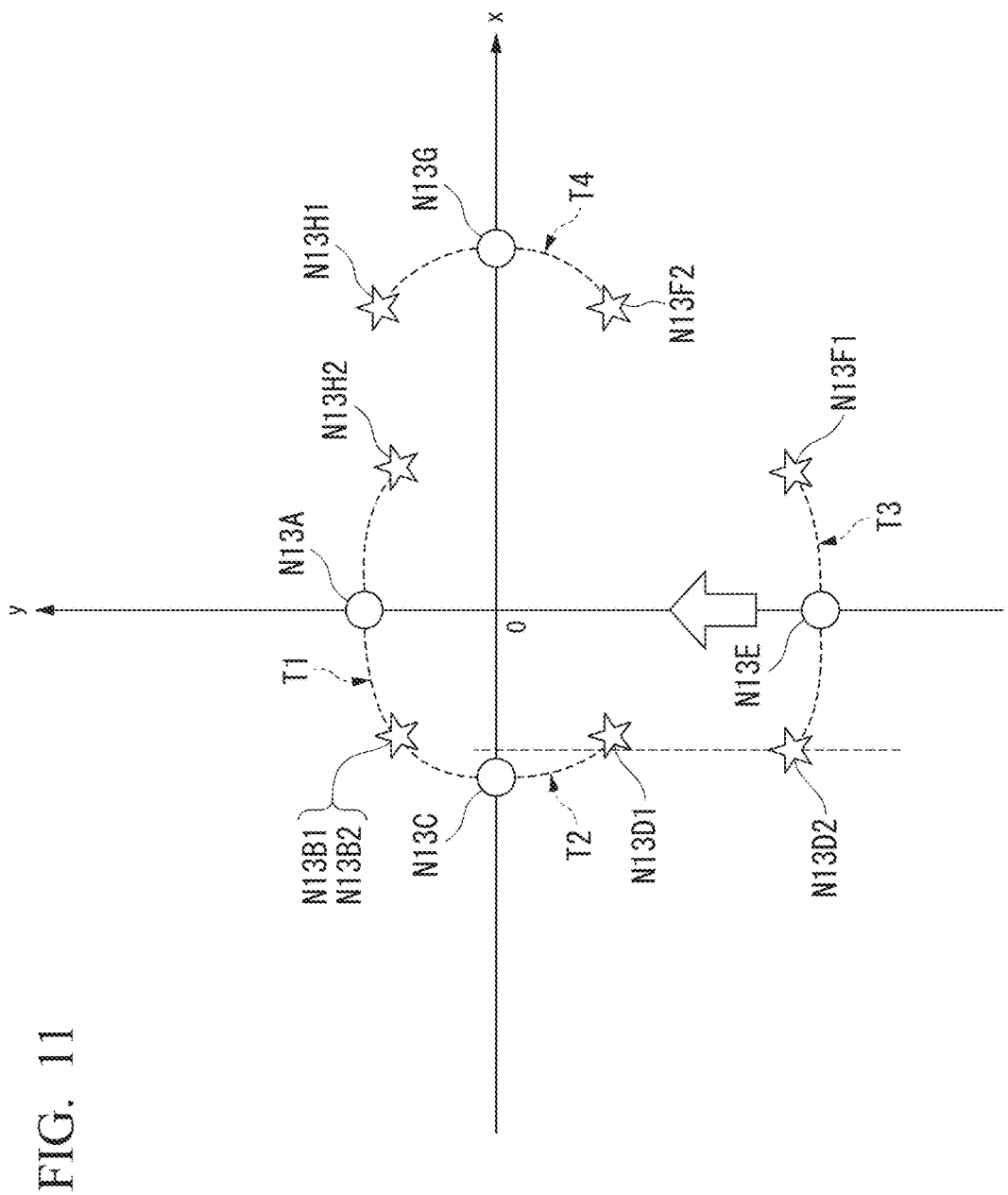
FIG. 11 is a fifth diagram illustrating specific content of a process of the contour estimation unit according to the first embodiment.

Next, FIG. 11 illustrates a process in which the contour estimation unit 202 causes positions of the subordinate points N13D1 and N13D2 indicating the position of the same strain gauge 13D to match by changing a coordinate position of each point included in the bundle T3.

As illustrated in FIG. 11, the contour estimation unit 202 performs a process of changing a coordinate position of each point of the bundle T3 so that the subordinate point N13D2 of the bundle T3 is closest to the subordinate point N13D1 of the bundle T2 when the bundle T3 is moved in parallel along the y-axis. Also, because the coordinate position of the bundle T2 is already fixed in this step, coordinate positions of the subordinate points N13D1 and N13D2 do not completely match and have some error.

After this process, the contour estimation unit 202 further performs a process of changing a coordinate position of each point of the bundle T4 so that the subordinate point N13F2 of the bundle T4 is closest to the subordinate point N13F1 of the bundle T3 when the bundle T4 is moved in parallel along the x-axis. In this step, as described above, the coordinate positions of the subordinate points N13F1 and N13F2 do not completely match because the coordinate position of the bundle T3 is already fixed. Also, the coordinate positions of the subordinate point N13H1 of the bundle T4 and the subordinate point N13H2 of the bundle T1 do not match.

Accordingly, in this step, error amounts of coordinate positions at a pair of subordinate points N13B1 and N13B2, a pair of subordinate points N13D1 and N13D2, a pair of subordinate points N13F1 and N13F2, and a pair of subordinate points N13H1 and N13H2 become non-uniform. Consequently, the contour estimation unit 202 finely adjusts coordinate positions of the bundles T1 to T4 again so that an error amount of a coordinate position at a pair of subordinate points becomes regular. For example, the contour estimation unit 202 performs micro movement while the relative positional relation of each point included in the bundles T1 to T4 is maintained for each of the bundles T1 to T4 and stops micro movement at a point in time at which the error amount is uniform while calculating the error amount for every micro movement.

Figure 12:
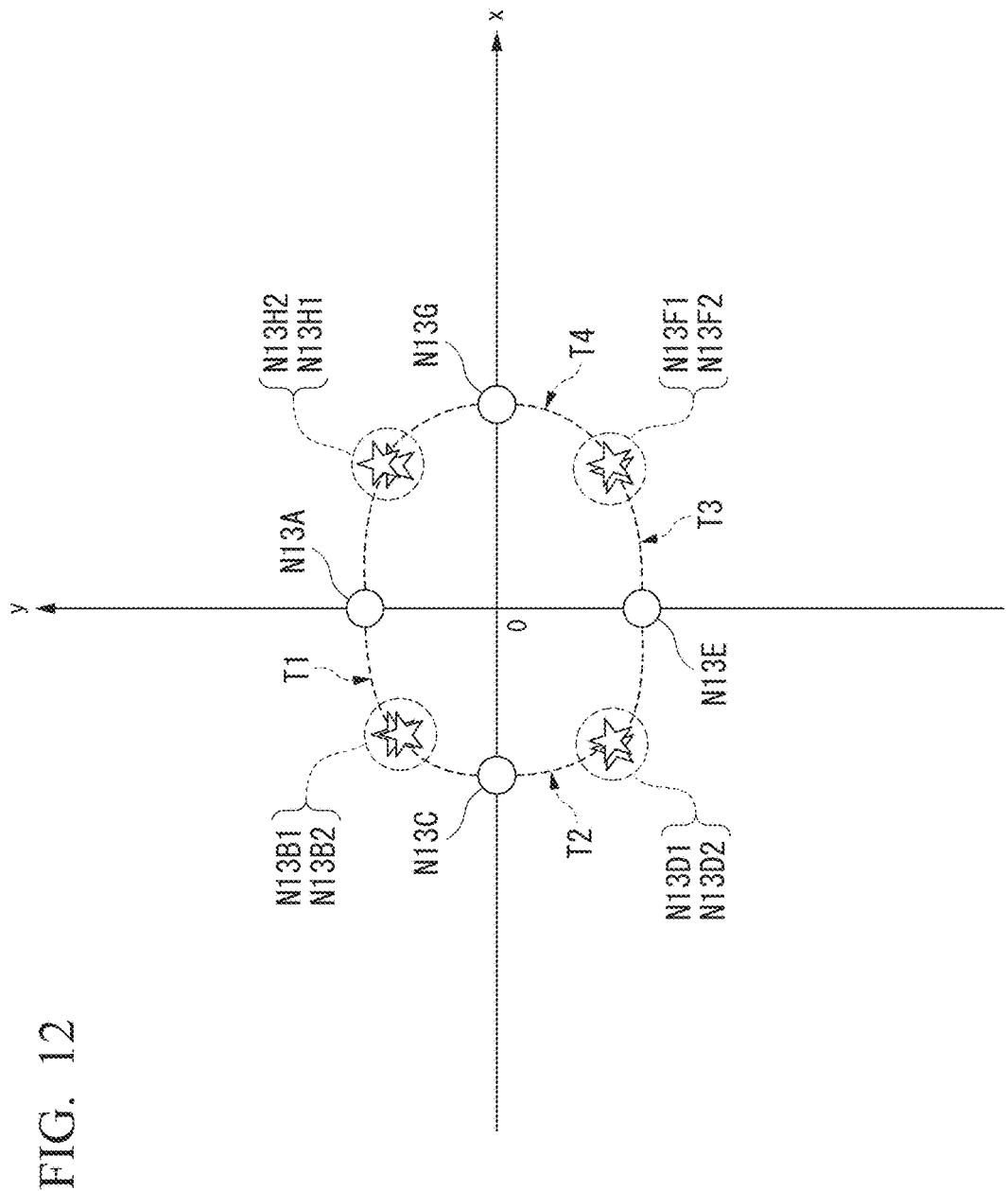
FIG. 12 is a sixth diagram illustrating specific content of a process of the contour estimation unit according to the first embodiment.

FIG. 12 illustrates a state immediately after parallel movement for the bundles T1 to T4 is completed.

As illustrated in FIG. 12, when error amounts of coordinate positions at a pair of subordinate points N13B1 and N13B2, a pair of subordinate points N13D1 and N13D2, a pair of subordinate points N13F1 and N13F2, and a pair of subordinate points N13H1 and N13H2 become uniform, final positions of the bundles T1 to T4 are specified.

The contour estimation unit 202 calculates a center point between coordinate positions indicated by the subordinate points N13B1 and N13B2 and specifies the coordinate position of the calculated center point as a point N13B indicating a position of the strain gauge 13B (the fourth step S13 in FIG. 6). The contour estimation unit 202 also performs a similar process on the other pairs of subordinate points (a pair of N13D1 and N13D2, a pair of N13F1 and N13F2, and a pair of N13H1 and N13H2).

Figure 13:
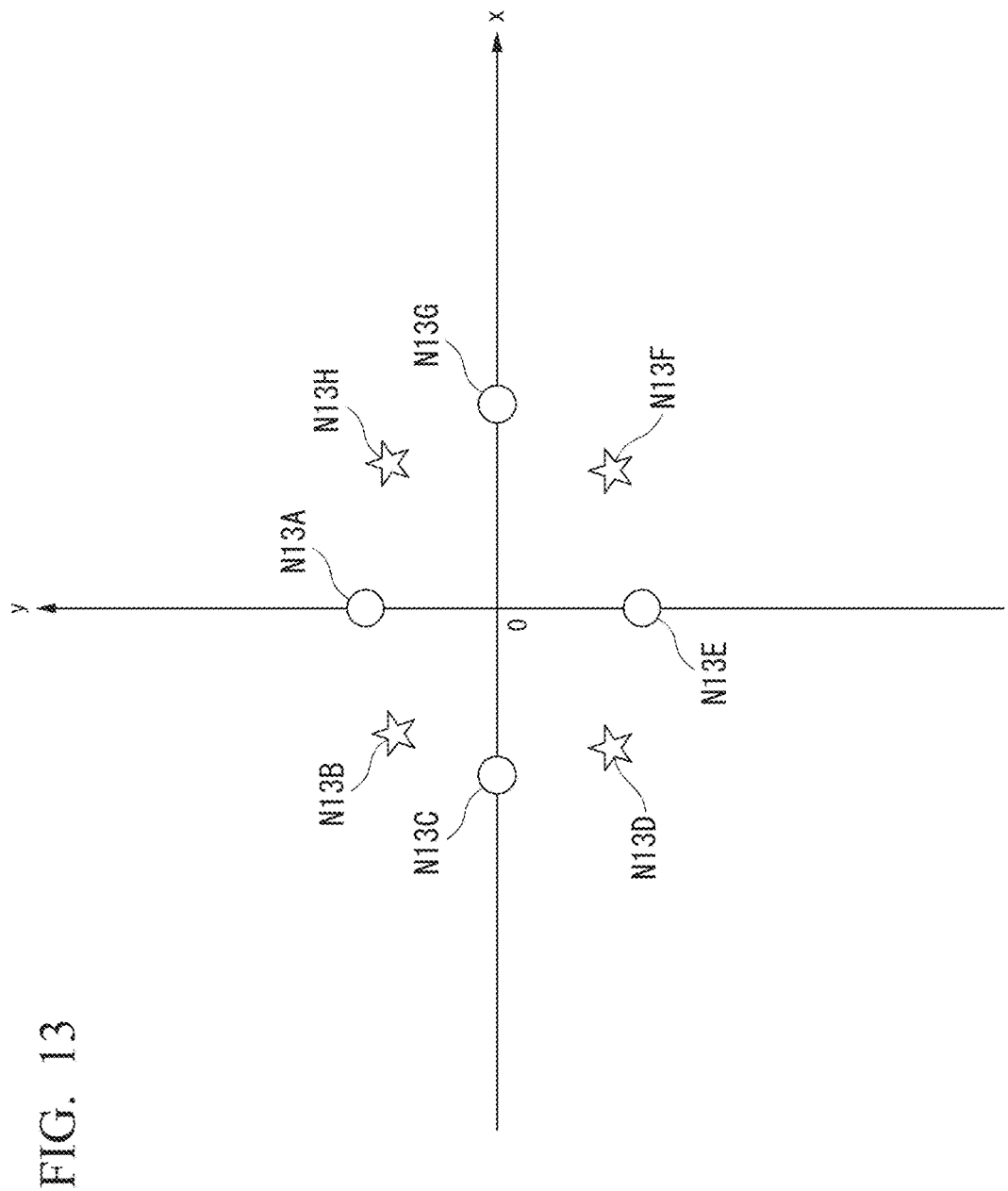
FIG. 13 is a seventh diagram illustrating specific content of a process of the contour estimation unit according to the first embodiment.

FIG. 13 illustrates a state immediately after a process of the above-described fourth step S13 is completed.

As illustrated in FIG. 13, the contour estimation unit 202 specifies points N13A to N13H indicating a relative positional relation between the strain gauges 13A to 13H on coordinates through processing of the relative position specifying process S1 (the first step S10 to the third step S12).

Also, in the process described using FIGS. 10 to 13, more generally, when coordinate positions of reference points (N13A to N13G) at which the bundles T1 to T4 are shown are moved in a direction of the origin O, coordinate positions after movement of the reference point and the subordinate point constituting each bundle are calculated so that a distance of a coordinate position of each subordinate point indicating the same strain gauge at each bundle of a state in which the relative positional relation between the reference point and the subordinate point maintains the relative positional relation before the movement is closest. The contour estimation unit 202 specifies the center point between the subordinate points indicating the same strain gauge as a point indicating the position of the strain gauge.

(In Terms of Shape Specifying Process)

The contour estimation unit 202 according to this embodiment executes the shape specifying process S2 of specifying a contour shape of a measurement target portion X while coupling the strain gauges 13A to 13H by a predetermined function curve after a relative positional relation between the strain gauges 13A to 13H is specified by completing the relative position specifying process S1 (FIG. 6).

Figure 14A:
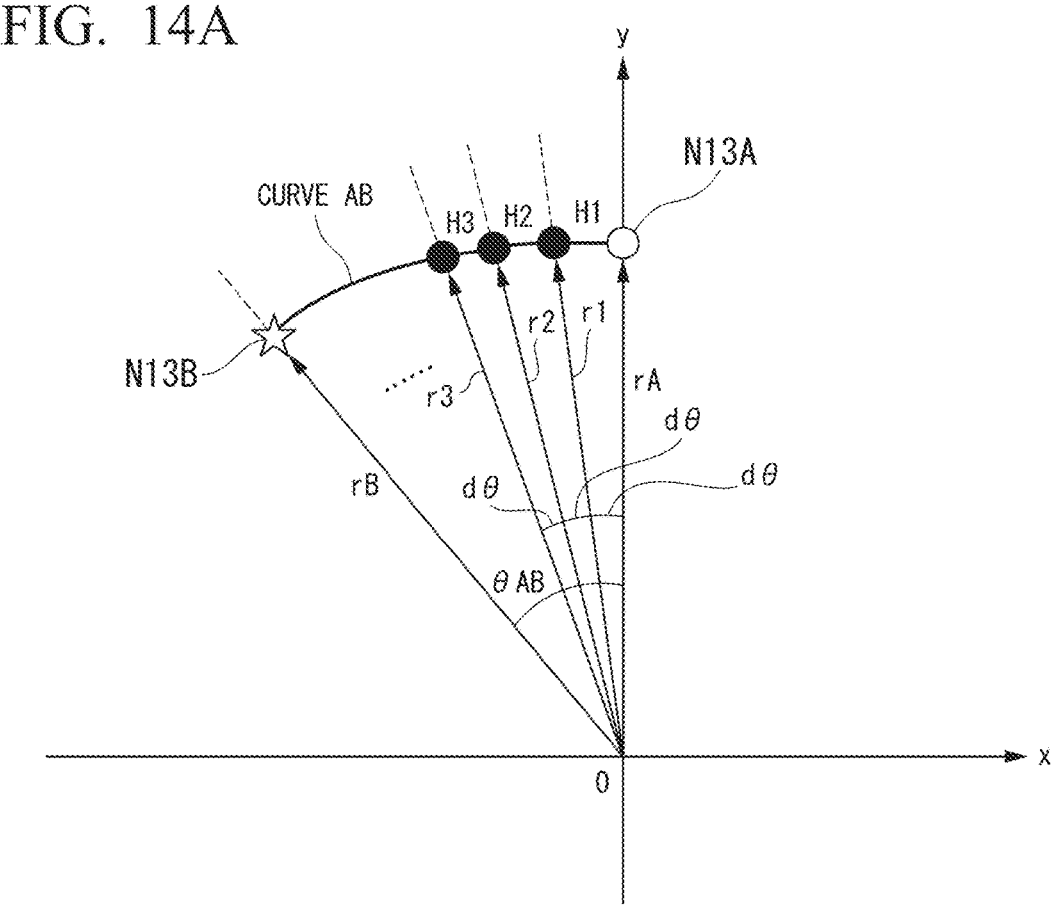
FIG. 14A is an eighth diagram illustrating specific content of a process of the contour estimation unit according to the first embodiment.
Figure 14B:
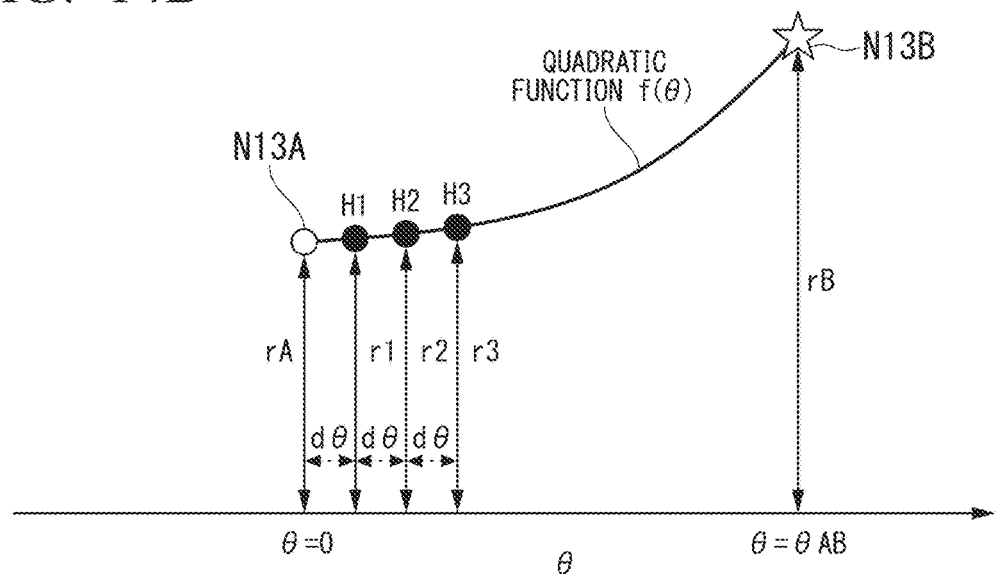
FIG. 14B is an eighth diagram illustrating specific content of a process of the contour estimation unit according to the first embodiment.

FIGS. 14A and 14B are diagrams illustrating a specific content of a processing of the shape specifying process S2.

As illustrated in FIG. 14A, the contour estimation unit 202 specifies a curve AB connected between a point N13A indicating a position of a strain gauge 13A and a point N13B indicating a position of a strain gauge 13B adjacent to the strain gauge 13A. Here, the curve AB specified by the contour estimation unit 202 is obtained by estimating a shape of a contour between the strain gauge 13A and the strain gauge 13B.

Specifically, the contour estimation unit 202 performs a process of setting a plurality of complementary points H1, H2, . . . for specifying the curve AB between the point N13A and the point N13B.

First, the contour estimation unit 202 specifies an angle θAB formed by a line segment having a length rA connected between the point N13A and the origin O and a line segment having a length rB connected between the point N13B and the origin O with respect to the origin O (see FIG. 14A).

Next, the contour estimation unit 202 specifies a preset micro angle dθ after referring to the HDD 211. This micro angle dθ indicates an angle obtained by fine division by equally dividing the angle θAB into m equal parts (m is an integer of 2 or more). The contour estimation unit 202 specifies the complementary point H1 on a straight line obtained by inclining the line segment connected between the point N13A and the origin O by the micro angle dθ. Subsequently, the contour estimation unit 202 specifies the complementary point H2 on a straight line obtained by further inclining the line segment by the micro angle dθ. As described above, the contour estimation unit 202 specifies the complementary points H1, H2, . . . for a plurality of straight lines passing through the origin O specified for every micro angle dθ (see FIG. 14A) (step S20 in FIG. 6).

Here, the contour estimation unit 202 specifies positions of the complementary points H1, H2, . . . on the basis of a predetermined function (quadratic function f(θ)). This quadratic function f(θ) is a function of angles θ formed by the complementary points H1, H2, . . . , the origin O, and the point N13A indicating a position of the strain gauge 13A and specifies lengths r1, r2, . . . of the line segments connecting the complementary points H1, H2, . . . and the origin O as a solution.

Also, because coordinate positions of the point N13A and the point N13B are specified through the relative position specifying process S1, the contour estimation unit 202 calculates a distance rA between the point N13A and the origin O and a distance rB between the point N13B and the origin O from the specified coordinate positions. The contour estimation unit 202 sets the quadratic function f(θ) so that the constraint conditions of f(0)=rA and f(θAB)=rB are satisfied (see FIG. 14B).

For example, an angle formed by the complementary point H1, the origin O, and the point N13A indicating the position of the strain gauge 13A is dθ. Consequently, as illustrated in FIG. 14B, a length r1 of the line segment connecting the complementary point H1 and the origin O is calculated by r1=f(dθ). Likewise, a length r2 of the line segment connecting the complementary point H2 and the origin O is calculated by r2=f(2×dθ).

The contour estimation unit 202 specifies positions for all the complementary points H1, H2, . . . by iterating the above-described process (step S21 in FIG. 6).

Thus, the contour estimation unit 202 can specify a curve AB connecting the complementary points H1, H2, . . . . Likewise, the contour estimation unit 202 specifies all curves between other strain gauges such as a curve BC connecting the strain gauge 13B and the strain gauge 13C. The contour estimation unit 202 can finally specify a closed curve which connects all the strain gauges 13A to 13H, that is, a shape of a contour of the measurement target portion X.

(In Terms of Size Specifying Process)

The contour estimation unit 202 according to this embodiment executes a size specifying process S3 of specifying a size of a shape of a contour so that the size matches a size of a portion serving as an actual measurement target after the shape of the contour of the portion serving as the measurement target is estimated by completing the shape specifying process S2 (FIG. 6).

Specifically, the contour estimation unit 202 performs a process of enlarging or reducing the estimated contour shape so that a perimeter of the contour shape estimated in the shape specifying process S2 matches a separately measured perimeter of the measurement target portion X in the size specifying process S3 (step S30 in FIG. 6).

Here, the separately measured perimeter is a perimeter of the measurement target portion X, for example, actually measured using a measure or the like, separately from EIT measurement using the EIT measurement device 1.

Figure 15:
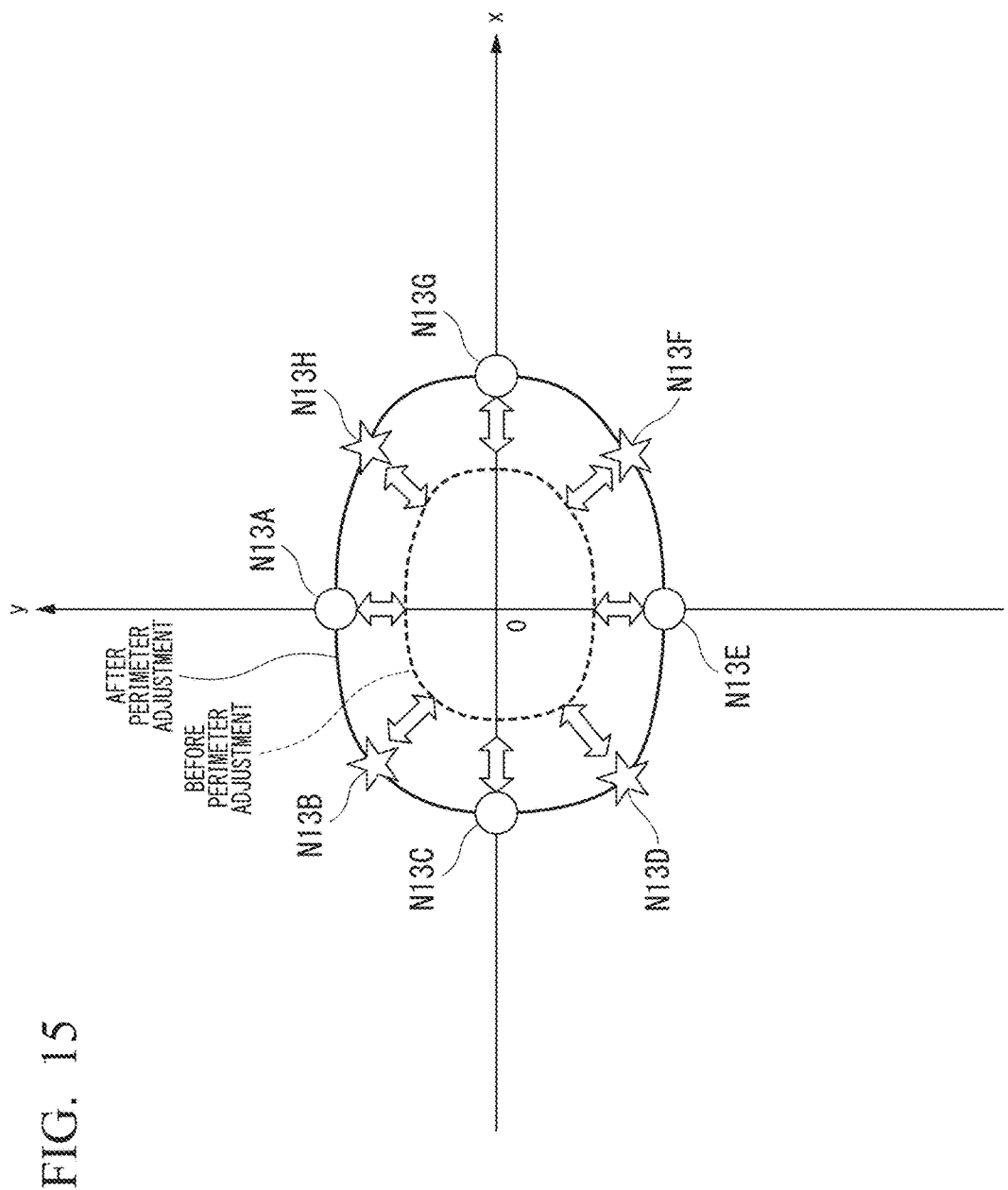
FIG. 15 is a ninth diagram illustrating specific content of a process of the contour estimation unit according to the first embodiment.

FIG. 15 illustrates a state of a process in which the contour estimation unit 202 enlarges or reduces the estimated contour shape.

The contour estimation unit 202 calculates the perimeter of the contour for which the shape is estimated in the shape specifying process S2 and compares the calculated perimeter with the perimeter of the measurement target portion X separately measured using the measure or the like. When the perimeter of the estimated contour is different from the actually measured perimeter, the perimeter of the estimated contour and the above-described actually measured perimeter are adjusted to match by enlarging or reducing the entire size while the estimated contour shape is maintained.

The contour estimation unit 202 estimates a contour shape of the measurement target portion X and a size of the contour shape through the above process.

(Effects)

Figure 16:
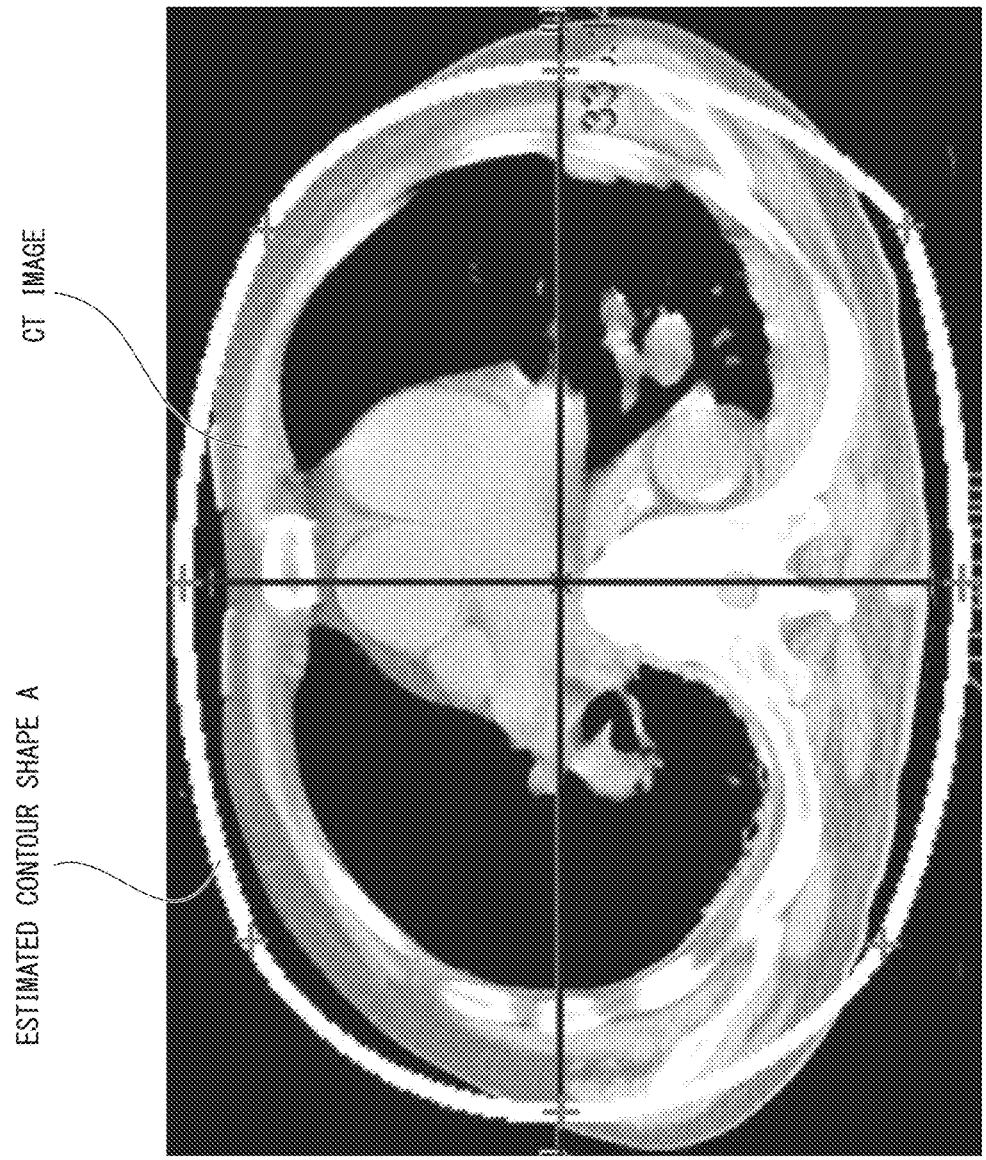
FIG. 16 is a diagram illustrating a processing result of the contour estimation unit according to the first embodiment.

FIG. 16 is a diagram illustrating a processing result of the contour estimation unit according to the first embodiment.

FIG. 16 illustrates a diagram in which a contour shape A of a thorax of a measurement target person estimated by the contour estimation unit 202 through the above-described processes S1 to S3 and a CT image acquired through a separate X ray CT of the thorax are superimposed. As illustrated in FIG. 16, a contour shape A estimated by the contour estimation unit 202 on the basis of the strain gauges 13A to 13H provided in the measurement belt 10 approximately matches a contour shape of the thorax shown in the CT image.

Figure 17A:
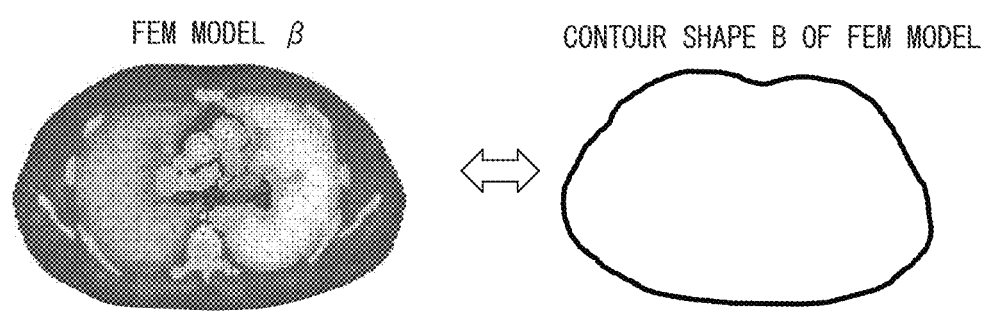
FIG. 17A is a diagram illustrating an example of an image generation process by the EIT measurement control unit according to the first embodiment.
Figure 17B:
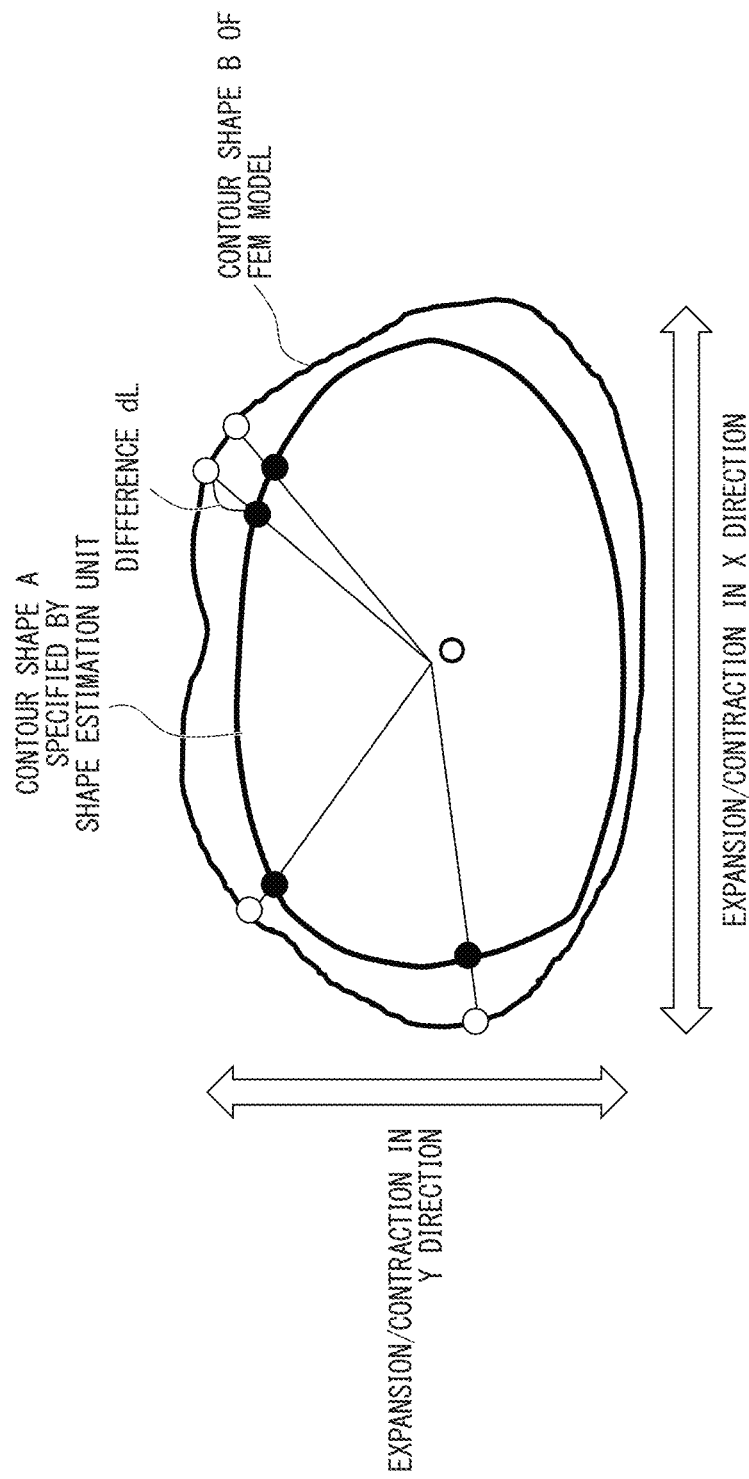
FIG. 17B is a diagram illustrating an example of an image generation process by the EIT measurement control unit according to the first embodiment.

FIGS. 17A and 17B are first and second diagrams illustrating examples of an image generation process by the EIT measurement control unit according to the first embodiment.

Here, a specific technique in which the EIT measurement control unit 201 generates a tomographic image on the basis of the contour shape A estimated by the contour estimation unit 202 will be briefly described. Here, the case in which the EIT measurement control unit 201 generates a tomographic image on the basis of the above-described finite element method is considered.

First, the EIT measurement control unit 201 designates a predetermined FEM model β (the left of FIG. 17A) pre-stored in the HDD 211. This FEM model β is pre-created on the basis of a CT image or the like of another measured person, and the same portion (for example, a chest portion) as that of the measurement target portion X in EIT measurement is designated. The EIT measurement control unit 201 superimposes the contour shape A estimated by the contour estimation unit 202 with the contour shape B (the right of FIG. 17A) of the designated FEM model β to compare the contour shapes A and B (see FIG. 17B).

Next, the EIT measurement control unit 201 performs a process of expanding/contracting the contour shape B at a fixed ratio in each of an X direction and a Y direction so that a difference between the contour shape A and the contour shape B is minimized. Specifically, the EIT measurement control unit 201 integrates a difference dL between a position of each point (a point indicated by a black dot in FIG. 17B) constituting the contour shape A and a point (a point indicated by a white dot in FIG. 17B) corresponding to each point indicated by the black dot on the contour shape B in the whole periphery and calculates an expansion/contraction ratio (rx, ry) for the X and Y directions in which an integrated value of the difference dL is minimized.

Subsequently, the EIT measurement control unit 201 applies the calculated expansion/contraction ratio (rx, ry) to the initially designated FEM model β and generates an FEM model β' expanded/contracted in each of the X direction and the Y direction at the same ratio.

The EIT measurement control unit 201 acquires a tomographic image based on a contour shape and a size of the measurement target portion X by applying a finite element method for the FEM model β' to voltage signals acquired via the electrode pads 12A to 12H.

Also, a plurality of different FEM model β1, β2, . . . created on the basis of CT images of a plurality of measured persons may be pre-stored in the HDD 211. In this case, the EIT measurement control unit 201 may perform a process of selecting an FEM model closest to the contour shape A estimated by the contour estimation unit 202. Specifically, the EIT measurement control unit 201 selects an FEM model βa having a perimeter matching the perimeter of the contour shape A, for example, in a chest portion, among the plurality of FEM models β1, β2, . . . An expansion/contraction process similar to that described above is performed on the FEM model βa in which the perimeter matches.

As described above, the operator can estimate a contour shape of a measurement target portion X in a measurement target person by merely wrapping the measurement belt 10 around the measurement target portion X using the EIT measurement device 1 and acquire a tomographic image based on the estimated contour shape.

Therefore, the operator can perform an accurate diagnosis on the basis of a tomographic image even when a shape or a size is different for every measurement target because it is possible to specify an absolute positional relation between the tomographic image and a portion serving as a measurement target.

According to the EIT measurement device according to the first embodiment, it is possible to simply perform a more accurate diagnosis even for various measurement targets having a different shape or size of a contour.

Also, the EIT measurement device 1 according to the first embodiment is not limited to the above-described aspect but can be modified as follows.

For example, a process in which the contour estimation unit 202 specifies a relative positional relation between the strain gauges 13A to 13H by moving the bundles T1 to T4 in parallel in the third step S12 (see FIGS. 10 to 12) is not limited to the content of the above-described process.

For example, the order in which the bundles T1 to T4 are moved in parallel by the contour estimation unit 202 is optional, and processing content is not particularly limited as long as a shift from the state illustrated in FIG. 9 to the state illustrated in FIG. 12 is possible.

Also, the contour estimation unit 202 is assumed to estimate a contour between points indicating the strain gauges 13A to 13H between which the relative positional relation is specified with a plurality of supplementary points on the basis of a quadratic function in step S21 of the shape specifying process S2 (see FIGS. 14A and 14B). However, as a modified example of this embodiment, a position of the supplementary point may be specified with another function (a linear function, a cubic function, or the like) besides the quadratic function. Also, a function of enabling a proper function or a necessary parameter to be appropriately selected from among a plurality of function candidates on the basis of an empirical rule or the like may be provided.

Also, according to the above description, an aspect in which the EIT measurement main body unit 20 is connected to the measurement circuit 11 of the measurement belt 10 via the signal cable 19 is provided. However, other modified examples of this embodiment are not limited to the aspect. For example, an aspect in which the EIT measurement main body unit 20 is mounted on the measurement circuit 11 may be provided.

In this case, the measurement circuit 11 equipped with the function of the EIT measurement main body unit 20 may further have a function of wireless or wired communication with an external device and a function of transmitting an acquired tomographic image to various terminal devices (a smartphone, a tablet type computer, a small size game machine, etc.) wirelessly or by wire.

Second Embodiment

Next, an EIT measurement device 1 according to the second embodiment will be described with reference to the drawings. Also, the same function components as those of the first embodiment are assigned the same reference signs and description thereof will be omitted.

Figure 18:
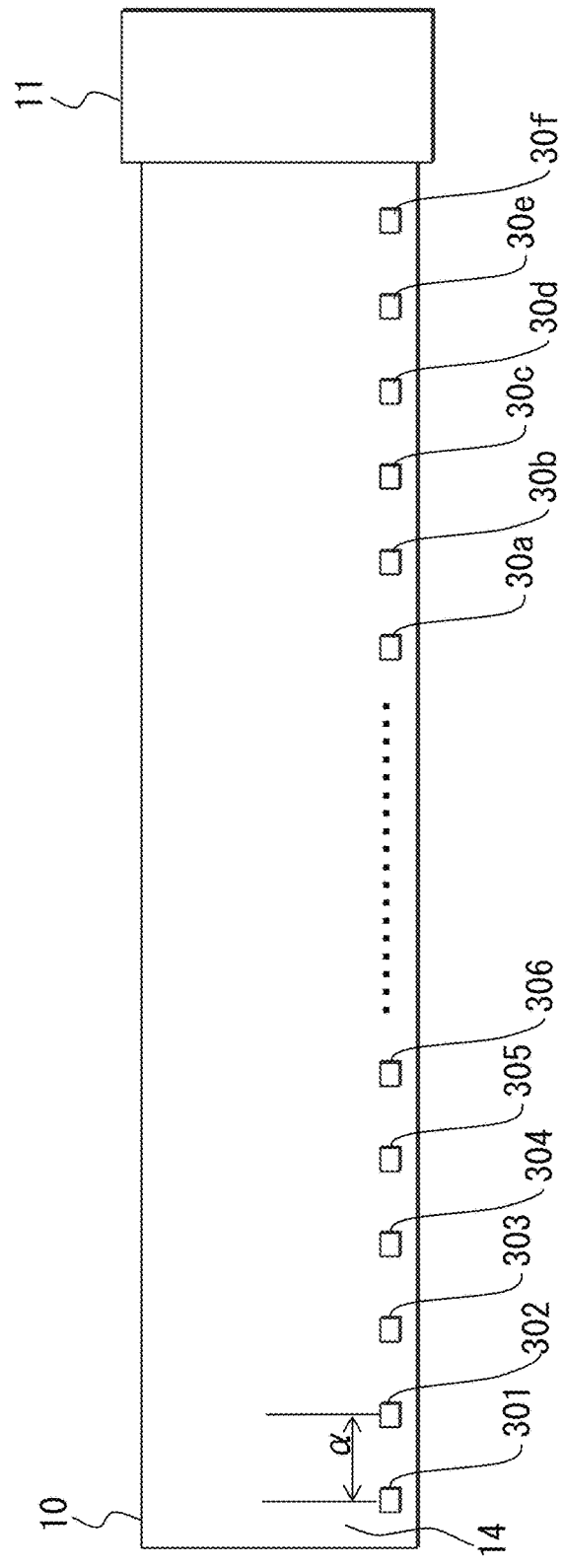
FIG. 18 is a diagram illustrating a functional configuration of a measurement belt according to a second embodiment.

FIG. 18 is a diagram illustrating a functional configuration of a measurement belt according to the second embodiment.

Also, the notation of electrode pads 12A to 12H and strain gauges 13A to 13H is omitted to avoid a complexity in the drawings in FIG. 18, but the electrode pads 12A to 12A and the strain gauges 13A to 13H are configured to be actually periodically arranged on a flexible substrate 14 as in the first embodiment.

As illustrated in FIG. 18, a measurement belt 10 according to this embodiment includes perimeter measurement electrode pads 301, 302, . . . , 30f attached to the measurement belt 10 and periodically arranged at intervals a in a longitudinal direction of the measurement belt 10 (in parallel to the electrode pads 12A to 12H or the like).

Figure 19:
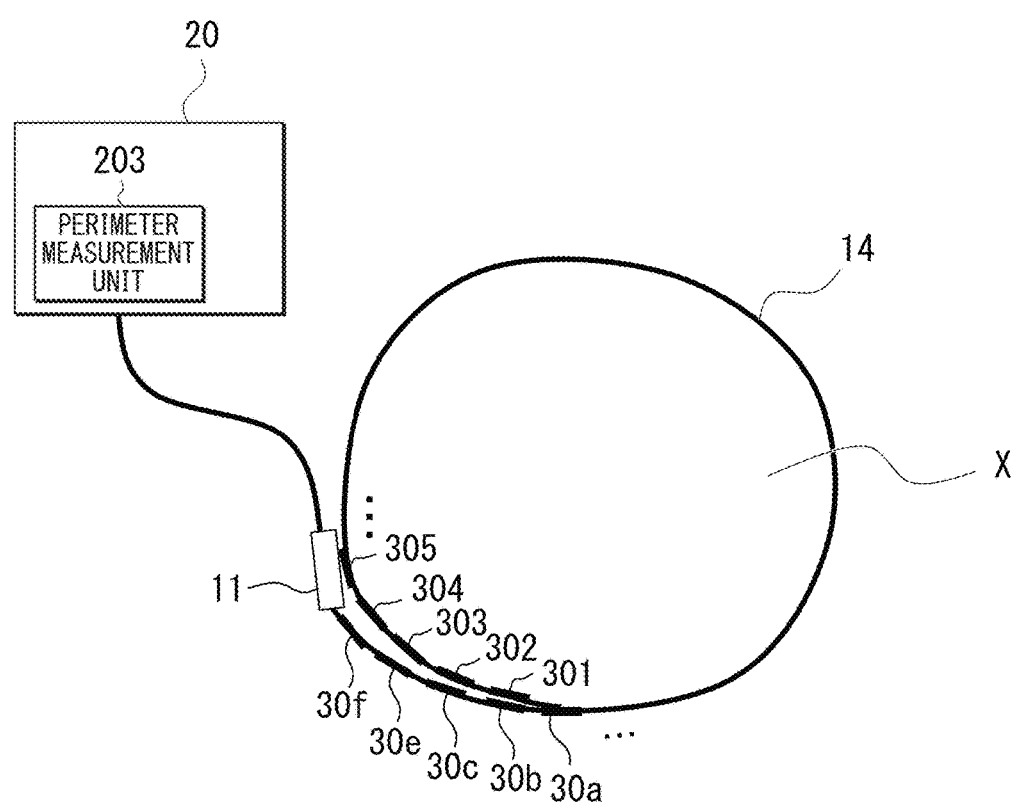
FIG. 19 is a diagram illustrating a function of a perimeter measurement unit according to the second embodiment.

FIG. 19 is a diagram illustrating a function of a perimeter measurement unit according to the second embodiment.

As illustrated in FIG. 19, the EIT measurement main body unit 20 according to this embodiment further includes a perimeter measurement unit 203. The perimeter measurement unit 203 has a function of measuring a perimeter of a measurement target portion X on the basis of a voltage signal acquired via the perimeter measurement electrode pads 301 to 30f. In terms of the perimeter measurement unit 203, an aspect in which a CPU 200 responsible for the overall operation of the EIT measurement main body unit 20 performs the function of the perimeter measurement unit 203 when a measurement program is executed as in the EIT measurement control unit 201 and the contour estimation unit 202 in the first embodiment may be provided.

The perimeter measurement unit 203 pre-recognizes intervals a (FIG. 18) of the perimeter measurement electrode pads 301 to 30f periodically pre-arranged on the measurement belt 10. The perimeter measurement unit 203 measures electrical impedance for every electrode pair in the perimeter measurement electrode pads 301 to 30f.

For example, because the perimeter measurement electrode pad 301 and the perimeter measurement electrode pad are in close contact with each other at the time of the state as illustrated in FIG. 19, the electrical impedance between the perimeter measurement electrode pads 301 and 30b is reduced on the basis of capacitance coupling of the two electrodes. Similar results are obtained even between 302 and 30c, 303 and 30e, and 304 and 30f which are other electrode pairs. On the other hand, because the perimeter measurement electrode pads 30a and 305 do not form capacitance coupling with other electrode pads, the perimeter measurement unit 203 detects high electrical impedance values for the perimeter measurement electrode pads 30a and 305.

Also, the interval a between the perimeter measurement electrode pads is not required to be absolutely the same as an interval between the electrode pads, and the perimeter length measurement accuracy can be improved by reducing the interval a.

Thus, the perimeter measurement unit 203 specifies a region where a position overlaps when the measurement belt 10 is wrapped from a difference of an electrical impedance value for each of pairs of the perimeter measurement electrode pads 301 to 30f and determines a perimeter of the measurement target portion X.

Because the EIT measurement device 1 can simultaneously acquire the perimeter of the measurement target portion X along with the EIT measurement, the operator of the EIT measurement device 1 can save time and trouble (see step S30 in FIG. 6) of actually and separately measuring the perimeter of the measurement target portion X using a measure or the like in the first embodiment.

Consequently, according to the EIT measurement device according to the second embodiment, it is possible to further simplify a procedure of performing EIT measurement.

Also, when the perimeter differs according to a measurement target person or a portion serving as a measurement target, for example, an aspect in which a plurality of measurement belts 10 for which a distance between electrode pads or the like changes are prepared, a measurement belt having an optimum length is selected from among the plurality of measurement belts 10, and the selected measured belt is used may be provided. Also, the measurement belt 10 may be provided with a stretchable mechanism (a rubber band or the like).

Also, the measurement belt 10 according to each embodiment is configured to have the eight electrode pads 12A to 12H and the eight strain gauges 13A to 13H periodically arranged in the longitudinal direction as described above, and content of the processes S1 to S3 in the contour estimation unit 202 has been described under the assumption that the number of arranged strain gauges 13A to 13H is eight.

However, an aspect in which the EIT measurement device 1 according to another embodiment, for example, has 16 or 32 electrode pads and 16 or 32 strain gauges may be provided. For example, when the measurement belt 10 is not provided with a stretchable mechanism, the number of electrode pads 12A to 12H in contact with the body surface of the measurement target portion X or the number of strain gauges 13A to 13H disposed in parallel to the electrode pads 12A to 12H among a plurality of electrode pads 12A to 12H or a plurality of strain gauges 13A to 13H pre-provided in the measurement belt 10 according to a size of the measurement target portion X is considered to change.

In this aspect, for example, the contour estimation unit 202 reads a coordinate position of a predetermined reference point indicating a position of a strain gauge designated for every predetermined interval at a distance of one or more strain gauges in a periodic arrangement on the measurement belt 10 from the HDD 211 and specifies the read coordinate position as initial coordinate values (first step S10).

Relative coordinate values specifying a coordinate position of a subordinate point indicating a position of any strain gauge arranged between strain gauges indicated by the reference point for a coordinate position of the reference point are calculated on the basis of the curvature data acquired via the strain gauge (second step S11).

Hereinafter, it is possible to specify the relative positional relation of each strain gauge by performing the third step S12 and the fourth step S13 described in the first embodiment.

Third Embodiment

As described above, in the relative position specifying process S1 according to the first embodiment, an EIT measurement device 1 arranges references points N13A and N13E on the x-axis and arranges reference points N13C and N13G on the y-axis orthogonal to the x-axis when virtual positions on the xy coordinates of alternately designated strain gauges (strain gauges 13A, 13C, 13E, and 13G (FIG. 2)) are provisionally determined (see FIG. 7). That is, the EIT measurement device 1 according to the first embodiment performs calculation under the assumption that four (strain gauges 13A, 13C, 13E, and 13G) of the strain gauges periodically arranged on the measurement belt 10 are constantly arranged on axes (x- and y-axes) orthogonal to each other when the measurement belt 10 is wrapped around the measurement target portion X.

However, the periodic intervals (distances P) between the strain gauges 13A to 13H periodically arranged in the measurement belt 10 are fixed and a perimeter of the measurement target portion X changes according to a physique of the measurement target person. Accordingly, some of the strain gauges 13A to 13H are not necessarily arranged on mutually orthogonal axes. Accordingly, the EIT measurement device 1 according to the first embodiment is likely to cause an error in a shape estimation result when some of the strain gauges are not located on mutually orthogonal axes.

On the other hand, the EIT measurement device 1 according to the third embodiment can precisely estimate a contour shape even when some of the strain gauges are not located on mutually orthogonal axes.

Hereinafter, the EIT measurement device 1 according to the third embodiment will be described in detail with reference to the drawings.

Figure 20:
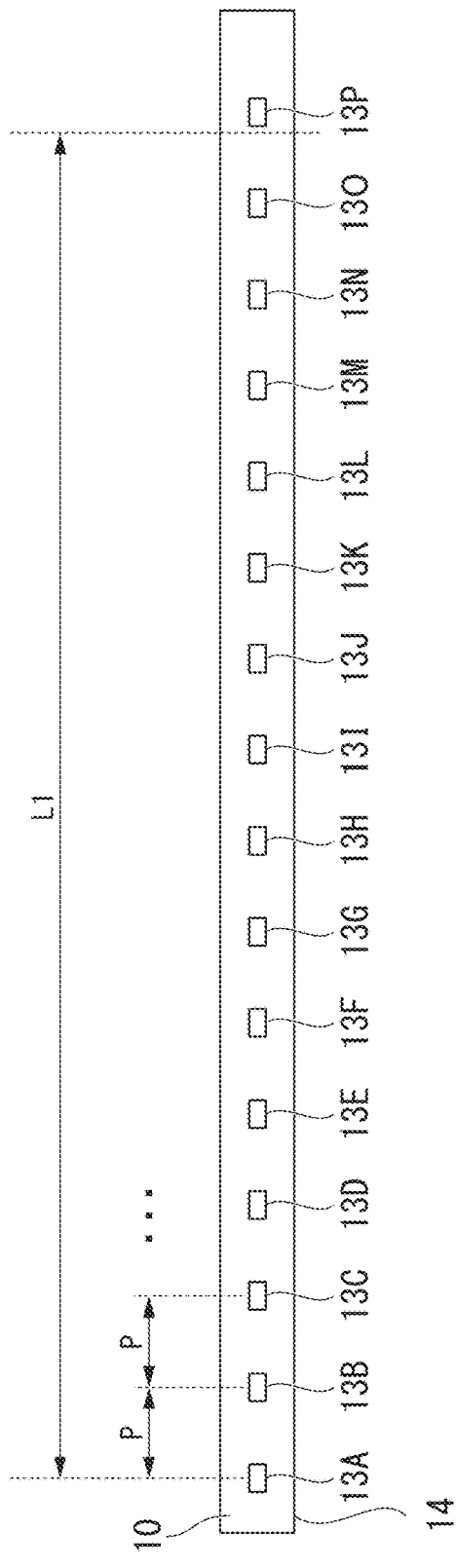
FIG. 20 is a diagram illustrating a functional configuration of a measurement belt according to a third embodiment.

FIG. 20 is a diagram illustrating a functional configuration of a measurement belt according to the third embodiment.

As illustrated in FIG. 20, in the measurement belt 10, sixteen strain gauges 13A to 13P are periodically arranged at distances P of regular intervals on a belt-shaped flexible substrate 14. Also, the notation of a measurement circuit 11 and electrode pads 12A to 12H is omitted to avoid a complexity of the drawings in FIG. 20, but the measurement circuit 11 and the electrode pads 12A to 12H are actually provided as in the first embodiment.

In the following description, the case in which the measurement belt 10 is wrapped around a chest portion of a chest circumference L1 serving as a measurement target object X will be described. Here, the chest circumference L1 has a length shorter than a length from the strain gauge 13A arranged at one end of the measurement belt 10 to the strain gauge 13P arranged at the other end (see FIG. 20).

Figure 21:
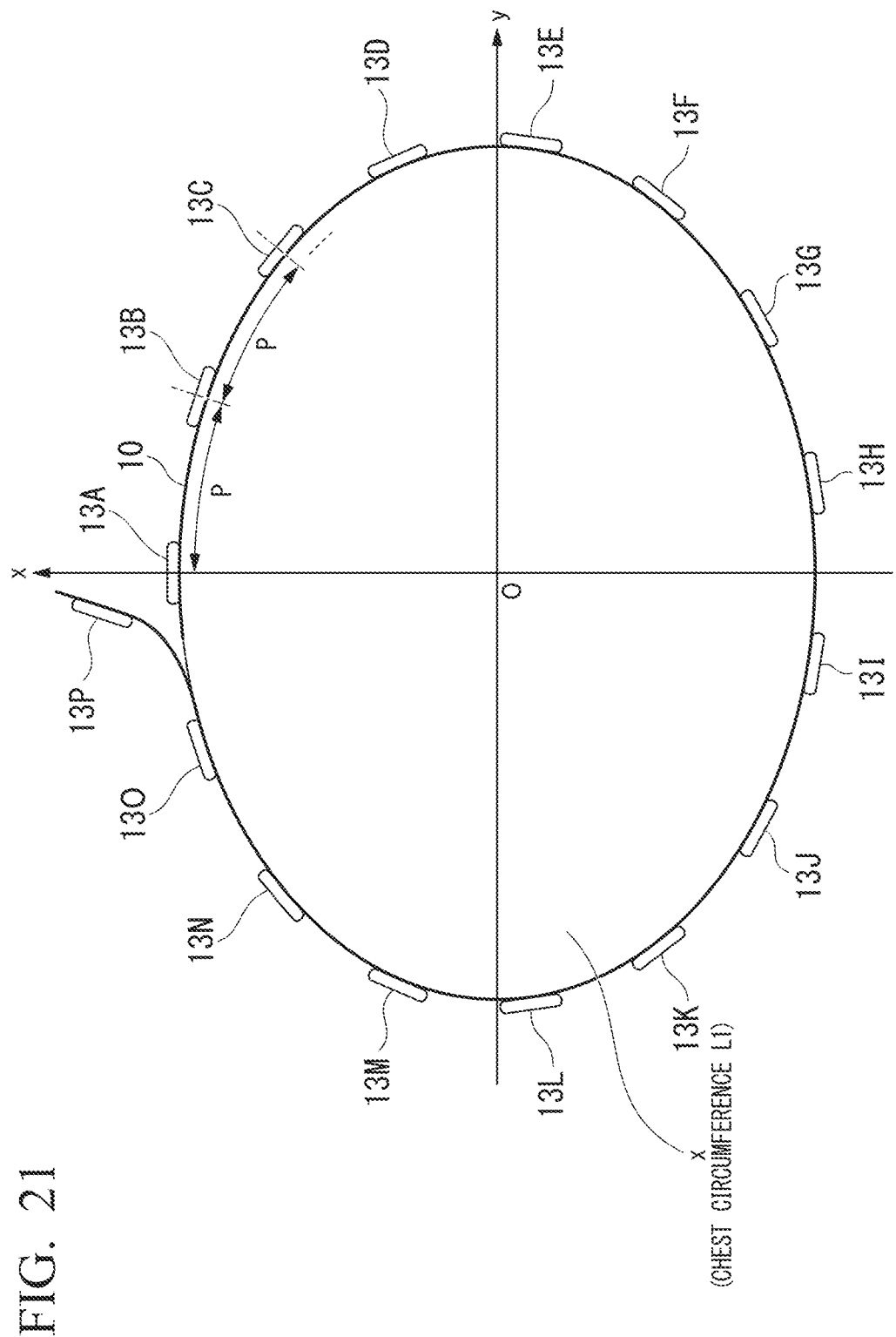
FIG. 21 is a diagram illustrating a state in which the measurement belt is wrapped according to the third embodiment.

FIG. 21 is a diagram illustrating a state in which the measurement belt is wrapped according to the third embodiment.

As illustrated in FIG. 21, the measurement belt 10 is wrapped while the strain gauge 13A arranged at the end of the measurement belt 10 is aligned with a center (sternum body) of the chest portion of the measurement target object X. In this case, because an integer multiple (16 times in this embodiment) of an interval (distance P) for each of the strain gauges 13A to 13P does not match the chest circumference L1, strain gauges other than the strain gauge 13A are arranged at positions shifted from the x-axis and the y-axis when the x-axis is defined as a symmetric axis in a front-back direction of the measurement target object X (measurement target person) and the y-axis is defined as a symmetric axis in a left-right direction.

Accordingly, as in the EIT measurement device 1 according to the first embodiment, an error occurs when a contour (thorax) estimation process is performed under the assumption that four of the strain gauges are constantly arranged on the x-axis and the y-axis which are mutually orthogonal.

Therefore, even in this case, the contour estimation unit 202 according to this embodiment executes the following process to enable the contour of the measurement target object X to be estimated with high precision.

Figure 22:
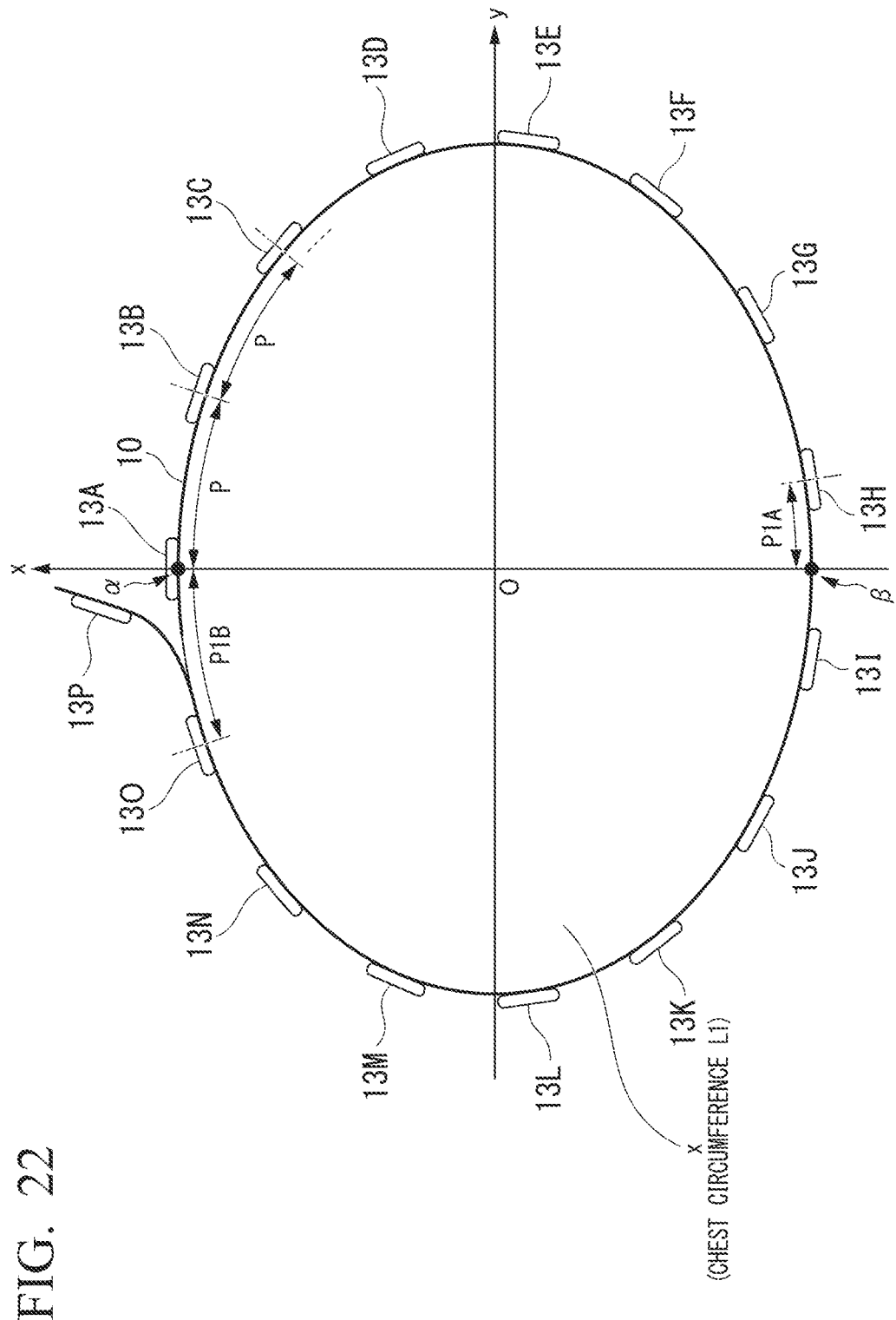
FIG. 22 is a diagram illustrating a function of a contour estimation unit according to the third embodiment.

FIG. 22 is a diagram illustrating a function of a contour estimation unit according to the third embodiment.

An operator who handles the EIT device 1 according to this embodiment first arranges the strain gauge (the strain gauge 13A in this embodiment) arranged at one end side of the measurement belt 10 at the center (on the sternum body) of the chest portion of the measurement target object X (measurement target person) as a first base point a.

Next, the operator wraps the measurement belt 10 around the measurement target object X while the first base point a in the measurement belt 10 is fixed on the sternum body of the measurement target object X.

When the chest circumference L1 of the measurement target object X does not match an integer multiple of a distance P as described above, the strain gauges 13A to 13P are arranged to be asymmetrical to the measurement target object X. Therefore, as illustrated in FIG. 22, no strain gauge is arranged at the center (spine protrusion) of the back of the measurement target object X. Therefore, the operator specifies a position on the measurement belt 10 matching a position of the spine protrusion of the measurement target object X as a second base point β. Specifically, the operator specifies a pair of strain gauges (strain gauges 13H and 13I in this embodiment) arranged with interleaving the spine protrusion of the measurement target object X among the strain gauges 13A to 13P. Further, the operator measures a distance P1A from the strain gauge (strain gauge 13H) to the spine protrusion (second base point β) of the measurement target object X.

Subsequently, when the measurement belt 10 is wrapped around the measurement target object X, the operator specifies a position of the strain gauge (the strain gauge 13O in this embodiment) closest to the first base point α among strain gauges in contact with the measurement target object X at the other end of the measurement belt 10. Specifically, the operator measures a distance P1B from the strain gauge 13O to the first base point a. Thereby, it is possible to specify a positional relation between strain gauges 13A to 13O on the measurement belt 10, the first base point a, and the second base point β which are prescribed separately.

Also, in this case, the strain gauge 13P arranged in the remaining portion of the other end of the measurement belt 10 is not used in a process of estimating a shape of a contour.

The contour estimation unit 202 of the EIT measurement device 1 according to this embodiment receives inputs of the distance P1A from the strain gauge 13H to the second base point β and the distance P1B from the strain gauge 13O to the first base point a measured by the operator. The operator manipulates the manipulation input unit 212 of the EIT measurement device 1 and inputs strain gauge identification information (information for specifying the strain gauges 13H and 13O) and information indicating the measured distances P1A and P1B to the EIT measurement device 1.

FIGS. 23 to 27 are first to fifth diagrams illustrating specific content of a process of the contour estimation unit according to the third embodiment.

Next, a process in which the contour estimation unit 202 according to this embodiment estimates a contour shape of a fault plane of the measurement target portion X will be specifically described.

(In Terms of Relative Position Specifying Process)

As in the first embodiment, the contour estimation unit 202 specifies the relative positional relation for each of the strain gauges 13A to 13O in the relative position specifying process S1.

Figure 23:
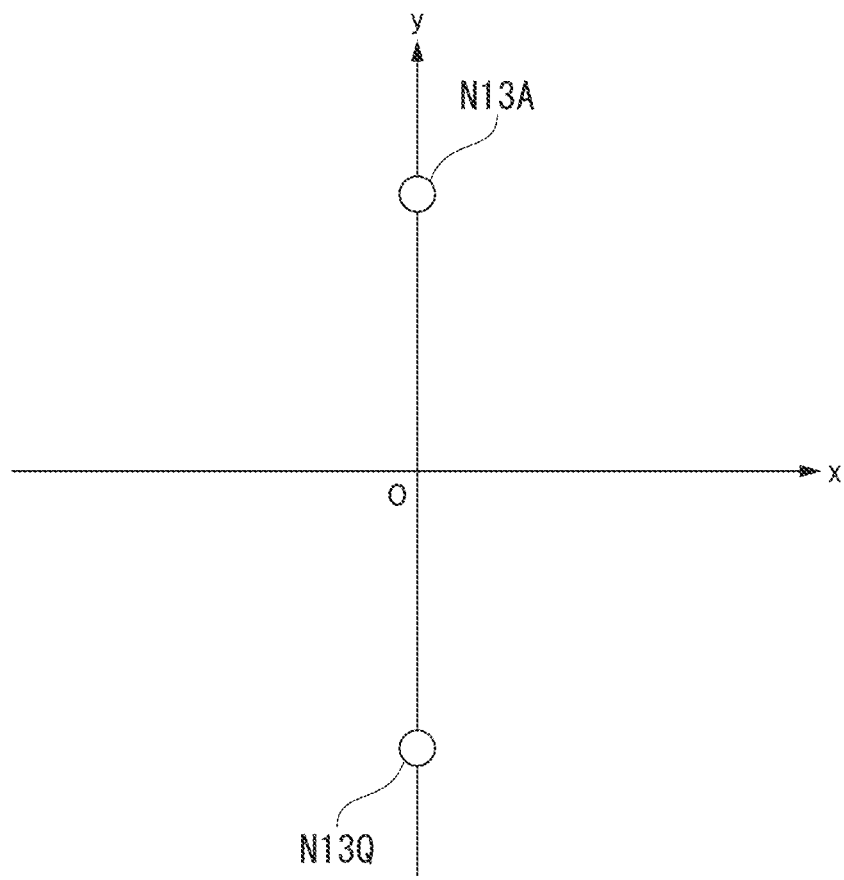
FIG. 23 is a first diagram illustrating specific content of a process of the contour estimation unit according to the third embodiment.

Specifically, as illustrated in FIG. 23, the contour estimation unit 202 first sets predetermined xy coordinates and provisionally determines a reference point N13A indicating a coordinate position on the xy coordinates for the strain gauge 13A on the xy coordinates by arranging the strain gauge 13A arranged at the first base point a on the y-axis in the first step S10 (FIG. 6).

Next, the contour estimation unit 202 provisionally determines a reference point on the xy coordinates corresponding to a strain gauge arranged at the second base point β. Here, no strain gauge is actually located on the second base point β (see FIG. 22). Accordingly, the contour estimation unit 202 regards a virtual strain gauge 13Q as being located at the second base point β and provisionally determines a reference point N13Q indicating a position of the virtual strain gauge 13Q on the y-axis. That is, both of the strain gauge 13A arranged on the first reference point a and the strain gauge 13Q (virtually) arranged on the second reference point β are arranged on the symmetric axis along the front-back direction of the measurement target object X, that is, the symmetric axis which connects the sternum body and the spine protrusion. Accordingly, the contour estimation unit 202 provisionally determines the position on the xy coordinates by designating that the reference point N13A and the reference point N13Q are located on the axis (y-axis) corresponding to the symmetric axis along the front-back direction of the measurement target object X.

As described above, in the first step S10 of the relative position specifying process S1, the contour estimation unit 202 according to this embodiment specifies a coordinate position of a reference point indicating the strain gauge 13A arranged on the symmetric axis of the measurement target object X (an axis connecting the sternum body and the spine protrusion) among a plurality of strain gauges 13A to 13P as predetermined initial coordinate values. In addition, the contour estimation unit 202 regards the virtual strain gauge 13Q as being arranged on the second base point β and executes the relative position specifying process S1 when no strain gauge is arranged at a position (second base point β) arranged on the above-described symmetric axis of the measurement target object X in the measurement belt 10 around which the measurement target object X is wrapped.

Here, the contour estimation unit 202 specifies coordinate positions of an upper reference point N13A and a lower reference point N13Q on the y-axis around the origin O. Specifically, the contour estimation unit 202 reads initial coordinate values pre-stored for each of the reference points N13A and N13Q from the HDD 211 to set the initial coordinate values on coordinates around the origin O. For example, initial coordinate values (0 [cm], 50 [cm]) for the reference point N13A, initial coordinate values (0 [cm], −50 [cm]) for the reference point N13Q, etc. are stored in the HDD 211.

Next, in the second step S11 (FIG. 6), the contour estimation unit 202 specifies a relative positional relation between the reference points N13A and N13Q and subordinate points indicating positions on the xy coordinates of two strain gauges arranged at both sides of the strain gauges 13A and 13Q corresponding to the reference points N13A and N13Q.

Also, the contour estimation unit 202 according to this embodiment defines a combination of one reference point (for example, the reference point N13A) and subordinate points (for example, N13B1, N13C1, N13D1, etc.) continuously arranged in series at both sides of the reference point associated through the above-described relative positional relation as a bundle of one set.

Here, strain gauges arranged to be adjacent to both sides of the strain gauge 13A are a strain gauge 13B and a strain gauge 13O (see FIGS. 21 and 22). In this case, the contour estimation unit 202 specifies positions on the xy coordinates of subordinate points N13B1 and N13O1 by designating a subordinate point indicating a relative position of the strain gauge 13B based on the position (xa, ya) of the reference point N13A as the subordinate point N13B1 and designating a subordinate point indicating a relative position of the strain gauge 13O based on the position of the reference point N13A as the subordinate point N13O1.

Also, strain gauges arranged to be adjacent to both sides of a virtual strain gauge 13Q are a strain gauge 13H and a strain gauge 13I (see FIGS. 21 and 22). In this case, the contour estimation unit 202 specifies positions on the xy coordinates of subordinate points N13H2 and N13I2 by designating a subordinate point indicating a relative position of the strain gauge 13H based on the position (xq, yq) of the reference point N13Q as the subordinate point N13H2 and designating a subordinate point indicating a relative position of the strain gauge 13I based on the position of the reference point N13Q as the subordinate point N13I2.

A process in which the contour estimation unit 202 according to this embodiment specifies a relative positional relation of subordinate points for the reference points N13A and N13Q is similar to that of the first embodiment (see FIG. 8).

However, the contour estimation unit 202 uses the fact that a distance from the reference point N13A to the subordinate point N13O1 is a distance P1B (<distance P) input by the operator when the relative position of the subordinate point N13O1 for the reference point N13A is specified. Specifically, the contour estimation unit 202 sets a point at which an integrated amount of a micro distance dP from the reference point N13A becomes a distance P1B as a subordinate point N13O1 in FIG. 8. Also, the contour estimation unit 202 uses the fact that a distance from the reference point N13A to the subordinate point N13B1 is a distance P when the relative position of the subordinate point N13B1 for the reference point N13A is specified.

Likewise, the contour estimation unit 202 specifies the relative position from the subordinate point N13H2 using the fact that a distance from the reference point N13Q to the subordinate point N13H2 is a distance P1A (<distance P) input by the operator. Specifically, the contour estimation unit 202 sets a point at which an integrated amount of a micro distance dP from the reference point N13Q becomes the distance P1A as the subordinate point N13H2 in FIG. 8.

Further, the contour estimation unit 202 specifies the relative position from the subordinate point N13I2 using the fact that a distance from the reference point N13Q to the subordinate point N13I2 is a distance (P-P1A). Specifically, the contour estimation unit 202 sets a point at which an integrated amount of a micro distance dP from the reference point N13Q becomes the distance (P-P1A) as the subordinate point N13I2 in FIG. 8.

Also, in the above-described case, the contour estimation unit 202 according to this embodiment specifies relative positions of the subordinate points N13H2 and N13I2 for the reference point N13Q under the assumption that the curvature acquired by the virtual strain gauge 13Q arranged at the second base point β is zero (a curvature radius is infinite).

Figure 24:
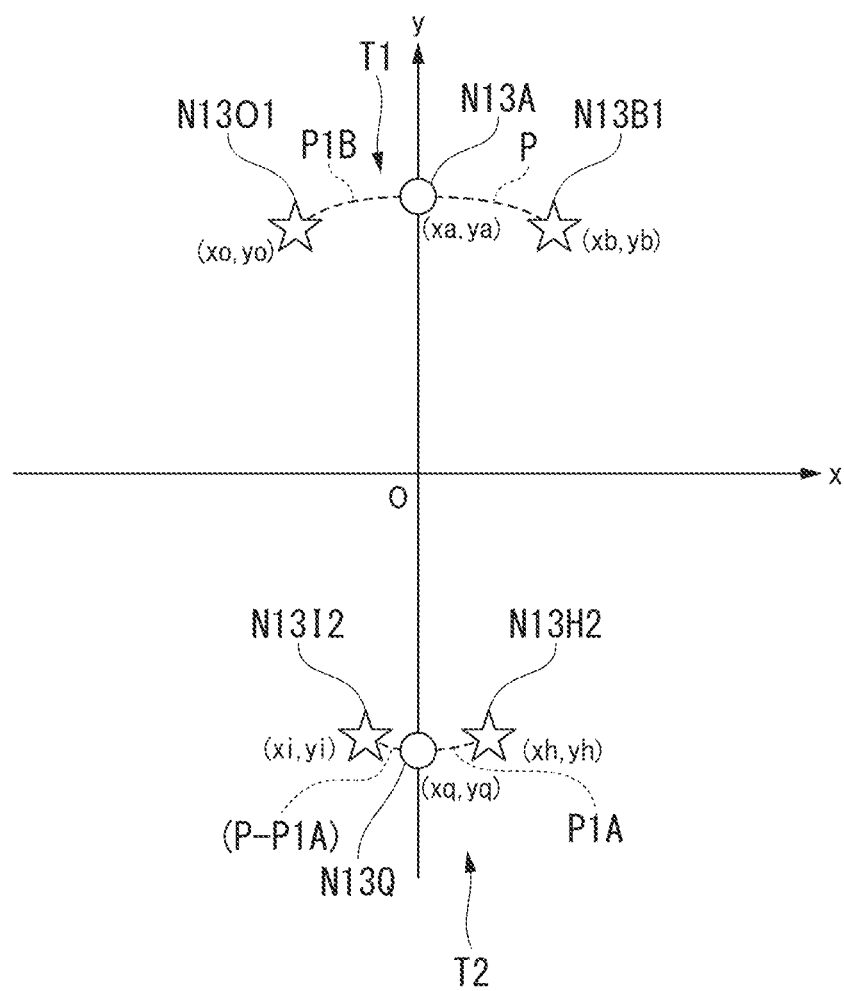
FIG. 24 is a second diagram illustrating specific content of a process of the contour estimation unit according to the third embodiment.
Figure 25:
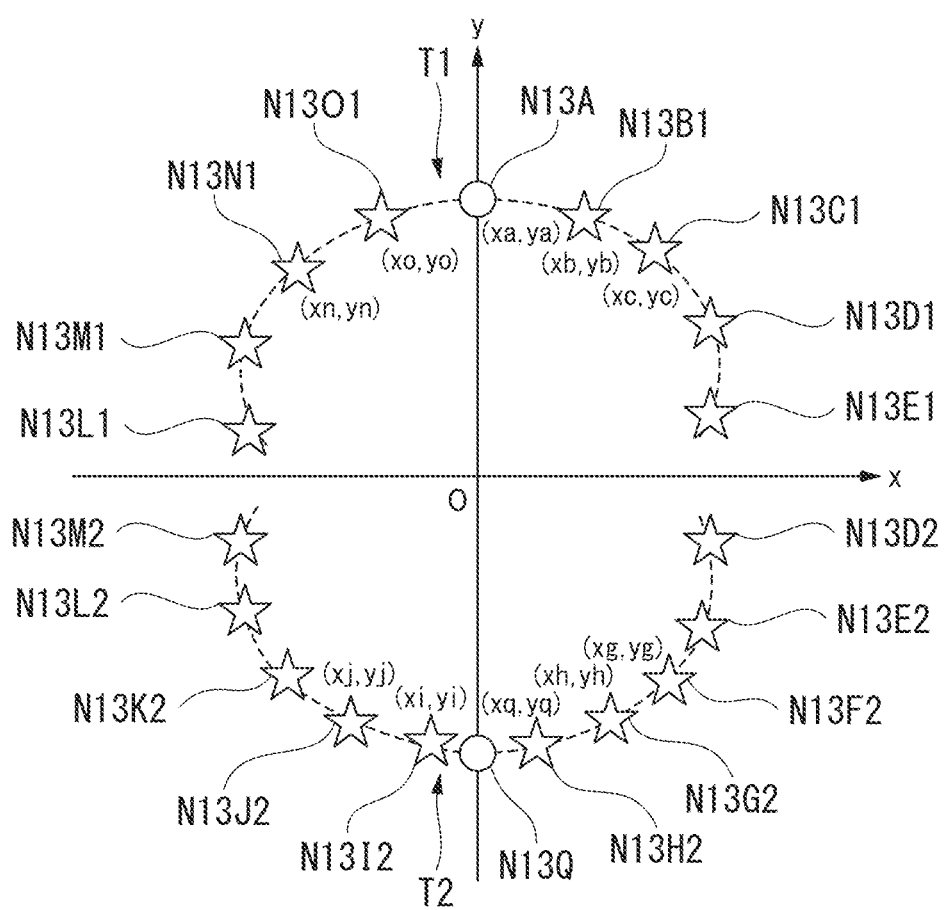
FIG. 25 is a third diagram illustrating specific content of a process of the contour estimation unit according to the third embodiment.

FIG. 24 illustrates a state in which the contour estimation unit 202 specifies positions of subordinate points adjacent to reference points N13A and N13Q on the basis of the reference points N13A and N13Q through the above process.

As illustrated in FIG. 24, the contour estimation unit 202 specifies a relative position (xb, yb) of the subordinate point N13B1 and a relative position (xo, yo) of the subordinate point N13O1 based on a position (xa, ya) of the reference point N13A. Likewise, the contour estimation unit 202 specifies a relative position (xh, yh) of the subordinate point N13H2 and a relative position (xi, yi) of the subordinate point N13I2 based on a position (xq, yq) of the reference point N13Q.

Further, the contour estimation unit 202 according to this embodiment specifies a position of a subordinate point further subordinate to each subordinate point by iterating the process illustrated in FIG. 8. For example, the contour estimation unit 202 specifies a position (xc, yc) of a subordinate point N13C1 (a subordinate point corresponding to the strain gauge 13C) adjacent to the subordinate point N13B1 based on a position (xb, yb) of the subordinate point N13B1. Likewise, the contour estimation unit 202 specifies a position (xn, yn) of a subordinate point N13N1 (a subordinate point corresponding to the strain gauge 13N) adjacent to the subordinate point N13O1 based on a position (xo, yo) of the subordinate point N13O1.

The contour estimation unit 202 specifies a position of each of subordinate points N13B1 to N13E1 which are subordinate in series at one side of the reference point N13A and a position of each of subordinate points N13L1 to N13O1 which are subordinate in series at the other side of the reference point N13A by iterating the above-described process. Thereby, a position of the bundle T1 around the reference point N13A is provisionally determined (see FIG. 25).

Likewise, the contour estimation unit 202 specifies a position (xg, yg) of a subordinate point N13G2 (a subordinate point corresponding to a strain gauge 13G) adjacent to the subordinate point N13H2 based on a position (xh, yh) of the subordinate point N13H2. Likewise, the contour estimation unit 202 specifies a position (xj, yj) of a subordinate point N13J2 (a subordinate point corresponding to a strain gauge 13J) adjacent to the subordinate point N13I2 based on a position (xi, yi) of the subordinate point N13I2.

The contour estimation unit 202 specifies a position of each of subordinate points N13D2 to N13H2 which are subordinate in series at one side of the reference point N13Q and a position of each of subordinate points N13I2 to N13M2 which are subordinate in series at the other side of the reference point N13Q by iterating the above-described process. Thereby, a position of the bundle T2 around the reference point N13Q is provisionally determined (see FIG. 25).

Here, as described above, subordinate points N13D1 and N13E1 belonging to the bundle T1 are points virtually indicating positions of the strain gauge 13D and the strain gauge 13E arranged on the measurement belt 10. On the other hand, subordinate points N13D2 and N13E2 belonging to the bundle T2 are also points virtually indicating positions of the strain gauge 13D and the strain gauge 13E arranged on the measurement belt 10.

That is, two subordinate points N13D1 and N13D2 belonging to different bundles (T1 or T2) indicate the position of the same strain gauge 13D. Also, two subordinate points N13E1 and N13E2 belonging to a different bundle indicate the position of the same strain gauge 13E. Likewise, two subordinate points N13L1 and N13L2 belonging to different bundles indicate the position of the same strain gauge 13L. Two subordinate points N13M1 and N13M2 belonging to different bundles indicate the position of the same strain gauge 13M.

Accordingly, in this case, it is considered that the subordinate points N13D1 and N13D2 are displayed at the same coordinate position, the subordinate points N13E1 and N13E2 are displayed at the same coordinate position, the subordinate points N13L1 and N13L2 are displayed at the same coordinate position, and the subordinate points N13M1 and N13M2 are displayed at the same coordinate position.

Consequently, the contour estimation unit 202 performs a process of moving positions on the xy coordinates by changing coordinate positions of points (reference points and subordinate points) included in the bundles T1 and T2 so that positions of subordinate points N13D1, N13E1, N13L1 and N13M1 included in the bundle T1 match positions of subordinate points N13D2, N13E2, N13L2, and N13M2 included in the bundle T2 in the third step S12 (FIG. 6). At this time, the contour estimation unit 202 changes (moves in parallel) coordinate positions of points while relative position relations between reference points and subordinate points included in the bundle T1 and the bundle T2 are maintained.

Figure 26:
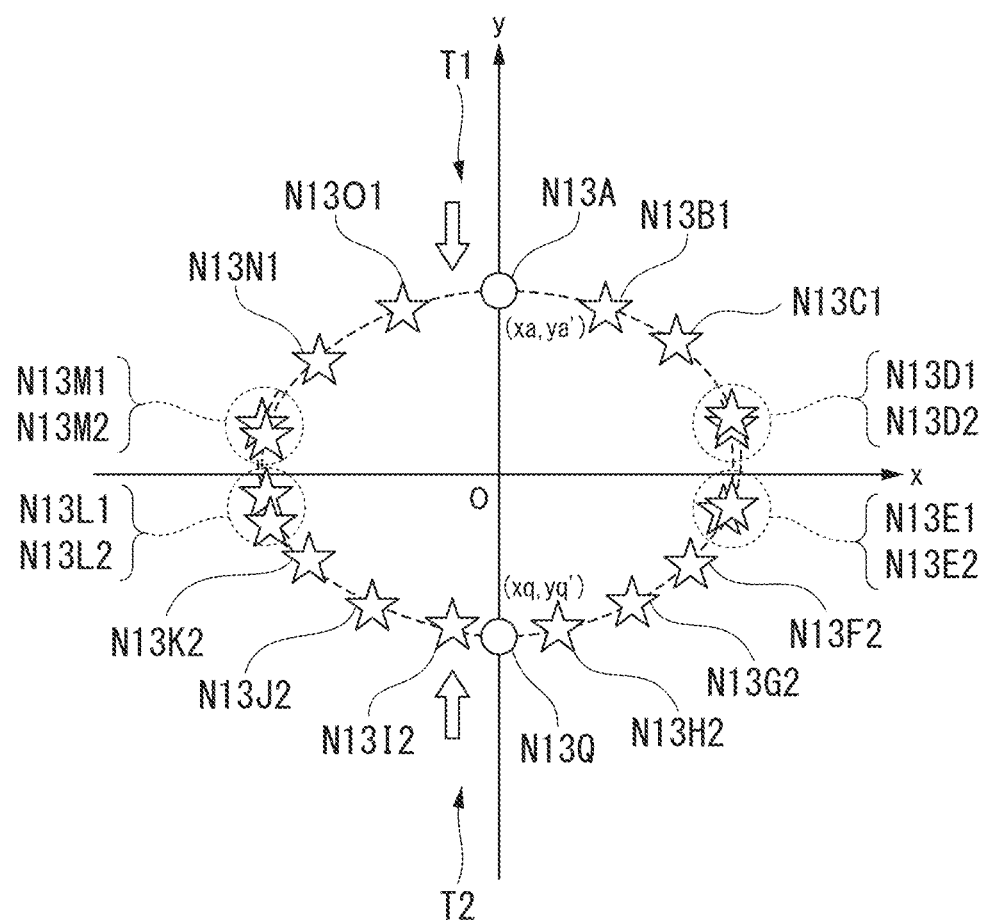
FIG. 26 is a fourth diagram illustrating specific content of a process of the contour estimation unit according to the third embodiment.

FIG. 26 illustrates a process in which the contour estimation unit 202 moves coordinate positions of points (reference points and subordinate points) included in the bundles T1 and T2 in parallel.

At this time, the contour estimation unit 202 moves the coordinate positions to positions at which a sum of errors of coordinate positions of the subordinate points N13D1 and N13D2 indicating the position of the same strain gauge 13D, coordinate positions of the subordinate points N13E1 and N13E2 indicating the position of the same strain gauge 13E, coordinate positions of the subordinate points N13L1 and N13L2 indicating the position of the same strain gauge 13L, and coordinate positions of the subordinate points N13M1 and N13M2 indicating the position of the same strain gauge 13M is minimized.

Specifically, the contour estimation unit 202 performs a process of changing coordinate positions so that the bundle T1 is moved in parallel in a −y direction along the y-axis. Here, the contour estimation unit 202 changes coordinates (xa, ya) of the reference point N13A of the bundle T1 to coordinate (xa, ya') (ya>ya'). Likewise, the contour estimation unit 202 performs a process of changing coordinate positions so that the bundle T2 is moved in parallel in a +y direction along the y-axis. Here, the contour estimation unit 202 changes coordinates (xq, yq) of the reference point N13Q of the bundle T2 to coordinate (xq, yq') (yq<yq').

As illustrated in FIG. 26, final positions of the bundles T1 and T2 are specified at positions at which a sum of errors of positions in a pair of N13D1 and N13D2, a pair of N13E1 and N13E2, a pair of N13L1 and N13L2, and a pair of N13M1 and N13M2 which are pairs of subordinate points belonging to a region in which the bundle T1 and the bundle T2 overlap is minimized.

Subsequently, the contour estimation unit 202 specifies a center point between subordinate points belonging to the bundles T1 and T2 indicating the same strain gauge as a point indicating a position of the strain gauge (step S13 (FIG. 16)).

Figure 27:
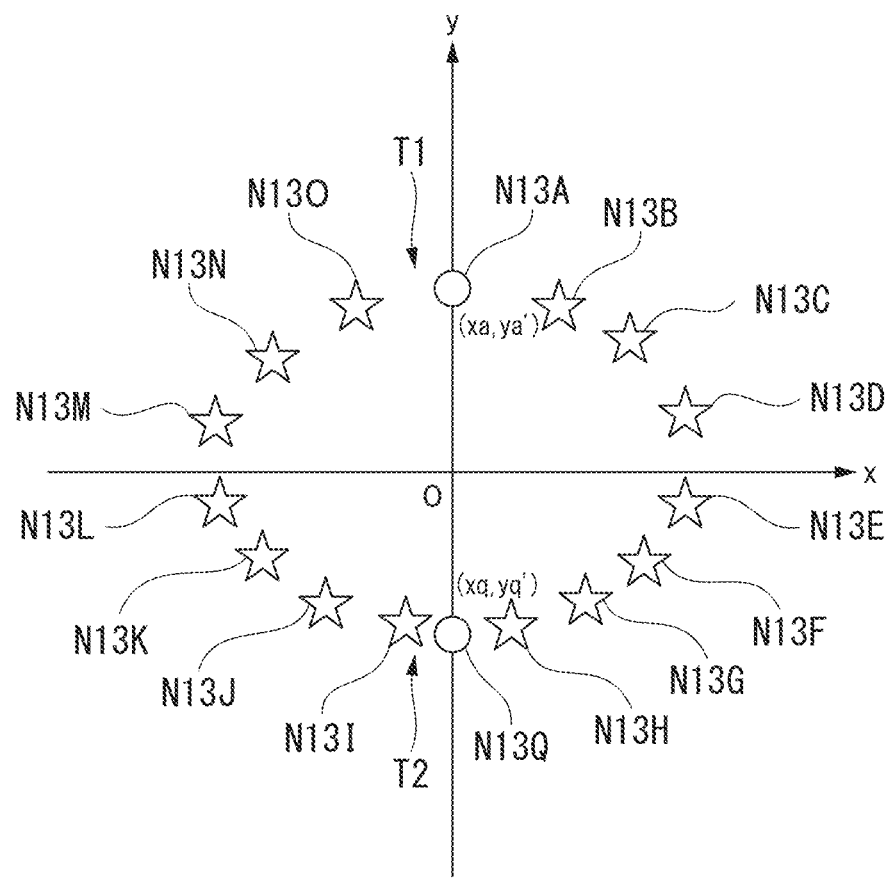
FIG. 27 is a fifth diagram illustrating specific content of a process of the contour estimation unit according to the third embodiment.

FIG. 27 illustrates a state immediately after the above-described fourth step S13 is completed. Also, in FIG. 27, the subordinate points N13B to N13O indicate positions on the xy coordinates corresponding to the strain gauges 13B to 13O. Here, the subordinate points N13B, N13C, N13N, and N13O have the same positions as those of the subordinate points N13B1, N13C1, N13N1, and N13O1 belonging to the bundle T1, respectively. Also, the subordinate points N13F, N13G, N13H, N13I, N13J, and N13K have the same positions as those of the subordinate points N13F2, N13G2, N13H2, N13I2, N13J2, and N13K2 belonging to the bundle T2, respectively. Subordinate points N13D, N13E, N13L, and N13M belonging to a region in which the bundles T1 and T2 overlap become a center position between the subordinate points N13D1 and N13D2, a center position between the subordinate points N13E1 and N13E2, a center position between the subordinate points N13L1 and N13L2, and a center position between the subordinate points N13M1 and N13M2 belonging to the bundles T1 and T2, respectively.

The contour estimation unit 202 specifies positions on the xy coordinates of fifteen strain gauges 13A to 13O (and a virtual strain gauge 13Q) through the processes of the above first step S10 to the fourth step S13.

Also, because the shape specifying process S2 and the size specifying process S3 subsequent to the relative position specifying process S1 are similar to those of the first embodiment, description thereof will be omitted.

(Effects)

As described above, the contour estimation unit 202 according to the third embodiment specifies a coordinate position of the strain gauge 13A arranged at a predetermined position (first base point a) on a symmetric axis (an axis which connects the sternum body and the spine protrusion) of the measurement target object X among a plurality of strain gauges 13A to 13P as predetermined initial coordinate values in the first step S10 of the relative position specifying process S1. In this case, the initial coordinate values become a predetermined position on the axis (y-axis) corresponding to the symmetric axis of the above-described measurement target object X.

Thereby, it is possible to precisely estimate a contour when the relative position specifying process S1 is executed as a constraint condition where the strain gauge 13A is arranged on the axis corresponding to the symmetric axis of the measurement target object X.

Also, the contour estimation unit 202 according to the third embodiment regards a virtual strain gauge 13Q as being arranged at a position on the symmetric axis of the measurement target object X and executes the relative position specifying process S1 when no strain gauge is arranged at a position (second base point β) on the symmetric axis of the measurement target object X on the measurement belt 10 wrapped around the measurement target object X. That is, the contour estimation unit 202 specifies a coordinate position of the virtual strain gauge 13Q (reference point N13Q) arranged at a position (second base point β) on the symmetric axis of the measurement target object X as predetermined initial coordinate values. In this case, the initial coordinate values also become a predetermined position on an axis (y-axis) corresponding to the symmetric axis of the measurement target object X.

Thereby, the contour estimation unit 202 executes the relative position specifying process S1 as a constraint condition where the virtual strain gauge 13Q is arranged on the axis corresponding to the symmetric axis of the measurement target object X. Thereby, even when no strain gauge is arranged on the symmetric axis of the measurement target object X if the measurement belt 10 is wrapped around the measurement target object X, it is possible to precisely estimate a contour.

Further, the contour estimation unit 202 separately acquires distances (distances P1A and P1B) between each of a plurality of strain gauges 13A to 13P arranged on the wrapped measurement belt 10 and the first base point a and between each of the plurality of strain gauges 13A to 13P and the second base point β. Using the acquired distances, the contour estimation unit 202 can precisely calculate relative coordinate values indicating a coordinate position of each subordinate point for coordinate positions of the reference points N13A and N13Q (for example, relative coordinate values of the subordinate points N13H2 and N13I2 for the reference point N13Q) in the second step S11.

Although the EIT measurement device 1 according to the third embodiment has been described in detail, a specific aspect of the EIT measurement device 1 according to this embodiment is not limited to the above description, but various design changes and modifications, etc. can be made without departing from the subject matter.

Figure 28:
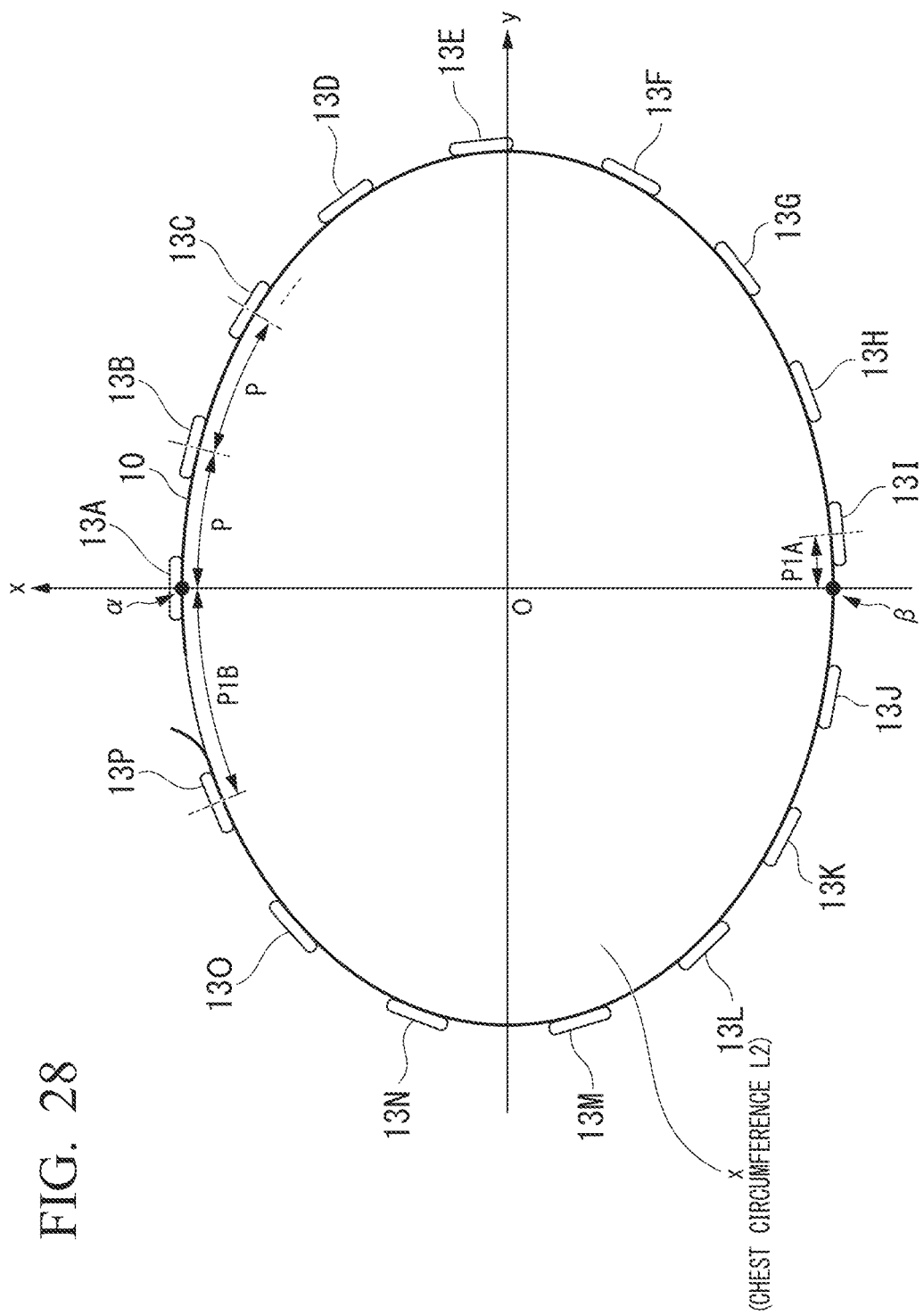
FIG. 28 is a diagram illustrating a state in which a measurement belt is wrapped according to a modified example of the third embodiment.

FIG. 28 is a diagram illustrating a state in which a measurement belt according to a modified example of the third embodiment is wrapped.

FIG. 28 illustrates the case in which the measurement belt 10 is wrapped around the chest portion of the chest circumference L2 serving as the measurement target object X. Here, a length of the chest circumference L2 is longer than a length from the strain gauge 13A arranged at one end of the measurement belt 10 to the strain gauge 13P arranged on the other end.

Even in this case, the measurement belt 10 is wrapped while the strain gauge 13A arranged at the end of the measurement belt 10 is aligned with a center (sternum body) of the chest portion of the measurement target object X. In this case, because an integer multiple (16 times in this embodiment) of an interval (distance P) for each of the strain gauges 13A to 13P does not match the chest circumference L2, strain gauges other than the strain gauge 13A are arranged at positions shifted from the x-axis and the y-axis when the x-axis is defined as a symmetric axis along a front-back direction of the measurement target object X (measurement target person) and the y-axis is defined as a symmetric axis along a left-right direction.

Accordingly, as in the EIT measurement device 1 according to the first embodiment, an error occurs when a contour (thorax) estimation process is performed under the assumption that four of the strain gauges are constantly arranged on the x-axis and the y-axis which are mutually orthogonal.

Even in this case, the operator specifies a position on the measurement belt 10 matching a position of the spine protrusion of the measurement target object X as a second base point β. Specifically, the operator specifies a pair of strain gauges (strain gauges 13I and 13J in this embodiment) arranged with interleaving the spine protrusion of the measurement target object X among the strain gauges 13A to 13P. Further, the operator measures a distance P1A from the strain gauge (strain gauge 13I) to the spine protrusion (second base point β) of the measurement target object X.

Subsequently, when the measurement belt 10 is wrapped around the measurement target object X, the operator specifies a position of the strain gauge (the strain gauge 13P in this embodiment) closest to the first base point a among strain gauges in contact with the measurement target object X at the other end side of the measurement belt 10. Specifically, the operator measures a distance P1B from the strain gauge 13P to the first base point a. Thereby, it is possible to specify a positional relation between the strain gauges 13A to 13P on the measurement belt 10 and the first base point a and the second base point β which are prescribed separately.

Hereinafter, it is possible to estimate a shape of a contour of the measurement target object X by executing a process similar to the process described in the third embodiment.

Therefore, it is possible to cope with a situation in one measurement belt 10 even when the chest circumference (chest circumference L2) of the measurement target object X is large. Thereby, it is possible to reduce the cost of the device because it is unnecessary to prepare a plurality of various types of measurement belts according to a physique of the measurement target object X (measurement target person).

Also, the case in which the operator measures a distance (distance P1A or P1B) from the first base point a or the second base point β to an adjacent strain gauge using the EIT measurement device 1 according to the third embodiment has been described.

However, an aspect in which the EIT measurement device 1 according to a modified example of the third embodiment automatically acquires the above-described distances P1A and P1B may be provided.

For example, the EIT measurement device 1 according to the modified example may include electrode pads periodically arranged at intervals more dense than intervals (distances P) at which the strain gauges 13A to 13P are arranged on the measurement belt 10. In this case, the EIT measurement device 1 acquires electrical impedance occurring between the periodically arranged electrode pads.

The EIT measurement device 1 detects a range in which the measurement belt 10 wrapped around the measurement target object X is in close contact with the measurement target object X on the basis of a change in the electrical impedance occurring between the periodically arranged electrode pads. Here, the impedance between the above-described electrode pads changes according to whether the measurement target object X which is a living body is in close contact with the electrode pad.

Thereby, the EIT measurement device 1 can automatically specify the strain gauge of the other end side arranged to be adjacent to the strain gauge (strain gauge 13A) of one end side and a distance P1B from the strain gauge of the other end side on the basis of a relative positional relation between the electrode pads in close contact with the measurement target object X and the strain gauges 13A to 13P.

Further, the EIT measurement device 1 may specify a position of the second base point β on the measurement belt 10 by detecting unique electrical impedance occurring between electrode pads arranged at a spine protrusion portion of the measurement target object X among the above-described periodically arranged electrode pads. Here, because the above-described electrode pad and a bone within the living body are in close contact in the spine protrusion portion of the measurement target object X, different unique electrical impedance is shown from electrode pads in contact with another portion of the measurement target object X. Thereby, the EIT measurement device 1 can automatically specify a position of the second base point β, a strain gauge adjacent to the second base point β, and a distance P1A from the strain gauge.

Also, although the case in which the EIT measurement device 1 according to the third embodiment specifies relative positions of subordinate points N13H2 and N13I2 for the reference point N13Q under the assumption that the curvature acquired by the virtual strain gauge 13Q arranged at the second base point β is zero has been described, the EIT measurement device 1 according to another embodiment is not limited to this aspect. For example, the EIT measurement device 1 may divide a distance between the subordinate point N13I2 and the subordinate point N13H2 into micro distances dP and obtain a curvature at a position corresponding to the reference point N13Q arranged between the subordinate point N13I2 and the subordinate point N13H2 by performing an interpolation using the curvature (actually measured value) acquired by each of the strain gauges 13I and 13H.

Also, although the EIT measurement devices 1 according to the first to third embodiments and their modified examples have been described to precisely estimate a shape of a contour of the measurement target object X on the basis of curvature data acquired from "strain gauges" (strain gauges 13A to 13P) periodically arranged on the measurement belt 10, the "strain gauge" is only one aspect for acquiring curvature data at a position at which each of the strain gauges is arranged. The EIT measurement device 1 according to the above-described embodiments does not need to necessarily use a strain gauge for acquiring curvature data, but may use another curvature sensor capable of acquiring curvature data. As an aspect of the curvature sensor, for example, a curvature sensor to which a conductive ink is applied, etc. are included. The curvature sensor using the conductive ink is manufactured using a change in electrical resistance of the conductive ink by expanding or contracting the conductive ink coated (printed) on a surface of a bendable substrate in accordance with bending of the substrate.

Also, the EIT measurement devices 1 according to the first to third embodiments and their modified examples in which all the electrode pads 12A, 12B, . . . and the strain gauges 13A, 13B, . . . are periodically arranged at regular intervals (intervals P) in the measurement belt 10 has been described, but the electrode pads 12A, 12B, . . . and the strain gauges 13A, 13B, . . . do not have to be periodically arranged in the EIT measurement device 1 according to another embodiment. That is, when intervals between the electrode pads 12A, 12B, . . . and the strain gauges 13A, 13B, . . . are known in the EIT measurement device 1 according to another embodiment, they may be arranged at mutually different intervals.

Also, the EIT measurement main body unit 20 according to each embodiment internally has a computer system as described above in the above description. A process of the processing in the above-described EIT measurement main body unit 20 is stored in a computer-readable recording medium in the form of a program. The above-described process is performed when a computer reads and executes the program. Here, the computer-readable recording medium is a magnetic disk, a magneto-optical disc, a compact disc read-only memory (CD-ROM), a semiconductor memory, or the like. In addition, the computer program may be distributed to the computer through a communication line, and the computer receiving the distributed program may execute the program.

While some embodiments of the present invention have been described above, these embodiments are examples of the invention and are not intended to limit the scope of the invention. These embodiments may be performed in various other forms and various omissions, substitutions, and changes can be made without departing from the subject matter of the present invention. These embodiments and modifications are also considered to be included in the scope and subject matter of the present invention and these are also included in the invention disclosed in the appended claims and its equivalent scope.

INDUSTRIAL APPLICABILITY

According to the above-described embodiments, it is possible to perform a simple and more accurate diagnosis even for various measurement targets each having a different shape or size of a contour.

REFERENCE SIGNS LIST

1 EIT MEASUREMENT DEVICE
10 MEASUREMENT BELT
11 MEASUREMENT CIRCUIT
12A to 12H ELECTRODE PAD
13A to 13P STRAIN GAUGE
14 FLEXIBLE SUBSTRATE
19 SIGNAL CABLE
20 EIT MEASUREMENT MAIN BODY UNIT

200 CPU
201 EIT MEASUREMENT CONTROL UNIT
202 CONTOUR ESTIMATION UNIT
203 PERIMETER MEASUREMENT UNIT
210 RAM
211 HDD
212 MANIPULATION INPUT UNIT
213 IMAGE DISPLAY UNIT
214 EXTERNAL INTERFACE
301 to 30f PERIMETER MEASUREMENT ELECTRODE PAD

The invention claimed is:

1. An electrical impedance tomography (EIT) measurement device comprising:
a measurement belt to which a plurality of electrode pads arranged in a row and a plurality of strain gauges arranged in parallel to the plurality of electrode pads are integrally adhered and configured to be used after being wrapped around a portion serving as a measurement target of a living body; and
a processor configured to:
acquire a tomographic image of the portion serving as the measurement target while applying a current to the plurality of electrode pads and acquiring a voltage signal generated between the electrode pads; and
estimate a contour shape of the portion serving as the measurement target and a size of the contour shape on the basis of curvature data acquired via the plurality of strain gauges,
wherein the processor is further configured to:
set coordinate positions of a plurality of reference points as predetermined initial coordinate values, each of the coordinate positions of the plurality of reference points indicating a position of one strain gauge among the plurality of strain gauges arranged in the row;
calculate relative coordinate values indicating coordinate positions of subordinate points according to the curvature data, the coordinate positions of the subordinate points indicating positions of one or more strain gauges with respect to the coordinate positions of adjacent reference points of the plurality of reference points, and the one or more strain gauges being disposed between the strain gauges indicated by the adjacent reference points of the plurality of reference points,
change coordinate positions of a first reference point and a second reference point different from the first reference point among the plurality of reference points such that coordinate positions between a first subordinate point and a second subordinate point becomes closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same strain gauge,
determine the coordinate positions of two subordinate points indicating positions of strain gauges disposed adjacently at both sides of each strain gauge indicated by each reference point as the coordinate position of a center point between the first subordinate point and the second subordinate point after the coordinate positions of the first reference point and the second reference point are changed; and,
estimate a contour shape and a size of the contour shape based on the relative positional relation of the positions of the reference and subordinate points using a predetermined function curve.

2. The EIT measurement device according to claim 1, wherein the processor is configured to enlarge or reduce the specified contour shape so that a perimeter of the estimated contour shape matches a separately measured perimeter of the portion serving as the measurement target after the contour shape is determined.

3. The EIT measurement device according to claim 1, wherein the processor is configured to determine the coordinate position of the reference point indicating the strain gauge arranged on a symmetric axis of the portion serving as the measurement target among the plurality of strain gauges as predetermined initial coordinate values when the coordinate positions of the plurality of reference points as predetermined initial coordinate values are set.

4. The EIT measurement device according to claim 3, wherein the processor is configured to regard the strain gauge as being arranged on the symmetric axis of the portion serving as the measurement target to determine a relative positional relation for the plurality of strain gauges, when no strain gauge is arranged at a position arranged on the true symmetric axis of the portion serving as the measurement target on the measurement belt wrapped around the portion serving as the measurement target.

5. The EIT measurement device according to claim 1, wherein the processor is configured to set a plurality of supplementary points for determining a curve connecting a position of one strain gauge and a position of another strain gauge adjacent to the one strain gauge when the contour shape is determined, and
wherein a distance from an origin of the plurality of supplementary points is determined by a predetermined function at an angle formed by the supplementary points, the origin, and the position of the one strain gauge.

6. The EIT measurement device according to claim 1, comprising:
a perimeter measurement electrode pad arranged in parallel to the plurality of electrode pads and adhered to the measurement belt; and
a perimeter measurement unit configured to measure a perimeter of the portion serving as the measurement target on the basis of a voltage signal acquired via the perimeter measurement electrode pad.

7. An EIT measurement method comprising:
winding a measurement belt to which a plurality of electrode pads arranged in a row and a plurality of strain gauges arranged in parallel to the plurality of electrode pads are integrally adhered around a portion serving as a measurement target of a living body;
acquiring a tomographic image of the portion serving as the measurement target while applying a current to the plurality of electrode pads and acquiring a voltage signal generated between the electrode pads;
determining a relative positional relation for every strain gauge;
estimating a contour shape of the portion serving as the measurement target and a size of the contour shape on the basis of curvature data acquired via the plurality of strain gauges;
wherein the specifying method further comprises:
setting specifying coordinate positions of a plurality of reference points as predetermined initial coordinate values, each of the coordinate positions of the plurality of reference points indicating a position of one strain gauge among the plurality of strain gauges arranged in the row;

calculating relative coordinate values indicating coordinate positions of subordinate points according to the curvature data, the coordinate positions of the subordinate points indicating positions of one or more strain gauges with respect to the coordinate positions of adjacent reference points of the plurality of reference points, and the one or more strain gauges being disposed between the strain gauges indicated by the adjacent reference points of the plurality of reference points, changing coordinate positions of a first reference point and a second reference point different from the first reference point among the plurality of reference points such that coordinate positions between a first subordinate point and a second subordinate point becomes closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same strain gauge;

specifying the coordinate positions of two subordinate points indicating positions of strain gauges disposed adjacently at both sides of each strain gauge indicated by each reference point as the coordinate position of a center point between the first subordinate point and the second subordinate point after the coordinate positions of the first reference point and the second reference point are changed; and, estimating a contour shape and a size of the contour shape based on the relative positional relation of the positions of the reference and subordinate points using a predetermined function curve.

8. A non-transitory storage medium storing a program for causing a computer of an EIT measurement device, which includes a measurement belt to which a plurality of electrode pads arranged in a row and a plurality of strain gauges arranged in parallel to the plurality of electrode pads are integrally adhered and configured to be used after being wrapped around a portion serving as a measurement target of a living body to:

acquire a tomographic image of the portion serving as the measurement target while applying a current to the plurality of electrode pads and acquiring a voltage signal generated between the electrode pads; and estimate a contour shape of the portion serving as the measurement target and a size of the contour shape on the basis of curvature data acquired via the plurality of strain gauges, wherein the program further causes the processor to:

set coordinate positions of a plurality of reference points as predetermined initial coordinate values, each of the coordinate positions of the plurality of reference points indicating a position of one strain gauge among the plurality of strain gauges arranged in the row;

calculate relative coordinate values indicating coordinate positions of subordinate points according to the curvature data, the coordinate positions of the subordinate points indicating positions of one or more strain gauges with respect to the coordinate positions of adjacent reference points of the plurality of reference points, and the one or more strain gauges being disposed between the strain gauges indicated by the adjacent reference points of the plurality of reference points;

change coordinate positions of a first reference point and a second reference point different from the first reference point among the plurality of reference points such that coordinate positions between a first subordinate point and a second subordinate point becomes closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same strain gauge;

determine the coordinate positions of two subordinate points indicating positions of strain gauges disposed adjacently at both sides of each strain gauge indicated by each reference point as the coordinate position of a center point between the first subordinate point and the second subordinate point after the coordinate positions of the first reference point and the second reference point are changed; and, estimate a contour shape and a size of the contour shape based on the relative positional relation of the positions of the reference points and subordinate points using a predetermined function curve.

9. An EIT measurement device comprising:

a measurement belt to which a plurality of electrode pads arranged in a row and a plurality of curvature sensors arranged in parallel to the plurality of electrode pads are integrally adhered and configured to be used after being wrapped around a portion serving as a measurement target of a living body; and a processor configured to:

acquire a tomographic image of the portion serving as the measurement target while applying a current to the plurality of electrode pads and acquiring a voltage signal generated between the electrode pads; and estimate a contour shape of the portion serving as the measurement target and a size of the contour shape on the basis of curvature data acquired via the curvature sensor, wherein the processor is further configured to: specify set coordinate positions of a plurality of reference points as predetermined initial coordinate values, each of the coordinate positions of the plurality of reference points indicating a position of one curvature sensor among the plurality of curvature sensors arranged in the row, calculate relative coordinate values indicating coordinate positions of subordinate points according to the curvature data, the coordinate positions of adjacent reference points of the subordinate points indicating positions of one or more curvature sensors with respect to the coordinate positions of the plurality of reference points, and the one or more curvature sensors being disposed between the curvature sensors indicated by the adjacent reference points the plurality of reference points, change coordinate positions of a first reference point and a second reference point different from the first reference point among the plurality of reference points such that coordinate positions between a first subordinate point and a second subordinate point becomes closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same curvature sensor determine the coordinate positions of two subordinate points indicating positions of curvature sensors disposed adjacently at both sides of each curvature sensor indicated by each reference point as the coordinate position of a center point between the first subordinate point and the second subordinate point after the coordinate positions of the first reference point and the second reference point are changed; and, estimate a contour shape and a size of a contour shape based on the relative positional relation of the positions of the reference points and subordinate points using a predetermined function curve.

\* \* \* \* \*